US012584924B2

(12) United States Patent
Li

(10) Patent No.: US 12,584,924 B2
(45) Date of Patent: Mar. 24, 2026

(54) COMPOSITIONS AND METHODS FOR DIAGNOSING AND TREATING CHRONIC KIDNEY DISEASE

(71) Applicant: SOCIÉTÉ DES PRODUITS NESTLÉ S.A., Vevey (CH)

(72) Inventor: Qinghong Li, Chesterfield, MO (US)

(73) Assignee: Societe des Produits Nestle S.A., Vevey (CH)

(*) Notice: Subject to any disclaimer, the term of this patent is extended or adjusted under 35 U.S.C. 154(b) by 751 days.

(21) Appl. No.: 18/085,795

(22) Filed: Dec. 21, 2022

(65) Prior Publication Data

US 2023/0204604 A1 Jun. 29, 2023

Related U.S. Application Data

(60) Provisional application No. 63/293,861, filed on Dec. 27, 2021.

(51) Int. Cl.
*G01N 33/68* (2006.01)

(52) U.S. Cl.
CPC ... *G01N 33/6893* (2013.01); *G01N 2800/347* (2013.01); *G01N 2800/56* (2013.01)

(58) Field of Classification Search
CPC ......... G01N 2570/00; G01N 2800/347; G01N 2800/56; G01N 33/50; G01N 33/6893
See application file for complete search history.

(56) References Cited

U.S. PATENT DOCUMENTS

| | | | | |
|---|---|---|---|---|
| 12,097,177 | B2 * | 9/2024 | Matsuura | A61K 31/343 |
| 2017/0122966 | A1 * | 5/2017 | Sabbisetti | G01N 33/57438 |
| 2018/0313851 | A1 * | 11/2018 | Abe | G01N 33/5308 |
| 2020/0292558 | A1 * | 9/2020 | Van Eyk | G01N 33/6848 |
| 2021/0373035 | A1 * | 12/2021 | Sarwal | C07K 16/44 |

FOREIGN PATENT DOCUMENTS

EP 3358347 A1 8/2018

OTHER PUBLICATIONS

Korman et al., "Feline CKD:Current Therapies—What is Achievable?", Journal of Feline Medicine and Surgery, vol. 15, Issue No. S1, Sep. 1, 2013, pp. 29-44, XP093024518.

Kongtasai et al., "Renal Biomarkers in Cats: A Review of the Current Status in Chronic Kidney Disease", Journal of Veterinary Internal Medicine, vol. 36, Issue No. 02, Feb. 26, 2022, pp. 379-396, XP093024432.

Tan et al., "Indoxyl Sulfate, a Valuable Biomarker in Chronic Kidney Disease and Dialysis", Hemodialysis International, vol. 21, Issue No. 02, Sep. 12, 2016, pp. 161-167, XP093024536.

Woolcock et al., "Feline Urinary F2—Isoprostanes Measured by Enzyme-Linked Immunoassay and Gas Chromatography-Mass Spectroscopy are Poorly Correlated", Journal of Veterinary Diagnostic Investigation, vol. 32, Issue No. 05, Jul. 5, 2020, pp. 648-655, XP055821717.

Ford et al., "Precision of a Clinical Metabolomics Profiling Platform for Use in the Identification of Inborn Errors of Metabolism", Appl Lab Med. Mar. 2020, pp. 342-356.

Li et al., "Metabolomics Analysis Reveals Deranged Energy Metabolism and Amino Acid Metabolic Reprogramming in Dogs With Myxomatous Mitral Valve Disease" J Am Heart Assoc. 2021 pp. 1-46.

International Search Report and Written Opinion to PCT/IB2022/062411 dated Apr. 18, 2023.

* cited by examiner

*Primary Examiner* — Kathryn Elizabeth Limbaugh
(74) *Attorney, Agent, or Firm* — K&L Gates LLP

(57) ABSTRACT

The present invention relates to methods and compositions for diagnosing and enabling treatment of chronic kidney disease in a feline. In one embodiment, a method of diagnosing chronic kidney disease (CKD) in a feline can comprise measuring a normalized relative abundance of a first urine biomarker and determining if the feline has CKD, early-stage CKD, or late-stage CKD based on the normalized relative abundance.

8 Claims, No Drawings

COMPOSITIONS AND METHODS FOR DIAGNOSING AND TREATING CHRONIC KIDNEY DISEASE

CROSS REFERENCE TO RELATED APPLICATIONS

This application claims the benefit of and priority to U.S. Provisional Application Ser. No. 63/293,861 filed Dec. 27, 2021, the disclosure of which is incorporated in its entirety herein by this reference.

BACKGROUND

The kidneys have five primary functions. They filter waste products from the body (e.g., urea and creatinine), regulate electrolytes (e.g., potassium, calcium, phosphorus, and sodium), produce erythropoietin (which stimulates bone marrow to produce red blood cells), produce rennin (which controls blood pressure), and produce and concentrate urine.

Chronic kidney disease ("CKD") is a progressive kidney disease which has four phases: loss of renal reserve, renal insufficiency, azotemia, and uremia. The kidneys have a large built-in reserve as only approximately 30% of kidney capacity is needed for normal kidney function. Kidney capacity diminishes with time for a variety of reasons, for example, advanced age and diseases and medications that damage the kidney(s). Renal insufficiency is characterized by decrease in renal function and is generally observed when about 70% of kidney function has been lost (i.e., when only about 30% of kidney capacity is available). Clinical signs are typically not obvious during the stages of loss of renal reserve and renal insufficiency, thereby making it difficult to detect CKD. Stage 1 CKD is nonazotemic and generally cannot be diagnosed as there are no overt clinical symptoms. Stage 2 CKD is mildly azotemic with clinical signs absent or mild. Stage 3 is moderately azotemic with clinical signs present. Stage 4 is severely azotemic with clinical signs present.

CKD is a terminal disease and is one of the leading causes of death in felines. Thus, there is a need for compositions and methods for diagnosing and preventing CKD in felines, especially diagnosing early-stage CKD. There is also a need for compositions and methods for treating CKD which provide partial or complete relief.

SUMMARY

The present disclosure relates generally to compositions and methods for diagnosing and treatment of chronic kidney disease in a feline. In one embodiment, a method of diagnosing chronic kidney disease (CKD) in a feline can comprise measuring a normalized relative abundance of a first urine biomarker selected from the urine biomarkers listed in Table 1 or Table 2 as described in Example 1. The method can further comprise determining that the feline has CKD if the normalized relative abundance of the first urine biomarker has a value outside the range under the non-CKD column, determining that the feline has early-stage chronic kidney disease if the normalized relative abundance of the first urine biomarker has a value in the range under the early-stage CKD column, or determining that the feline has late-stage CKD if the normalized relative abundance of the first urine biomarker has a value in the range under the late-stage CKD column.

In another embodiment, a method of enabling treatment or slowing progression of chronic kidney disease in a feline can comprise diagnosing chronic kidney disease (CKD) in the feline as discussed herein and recommending a composition for the feline, wherein the composition treats or slows the progression of CKD in the feline.

In still another embodiment, a feline urine biomarker for diagnosing early-stage chronic kidney disease (CKD) in a feline can be selected from the group consisting of sulfate, N-acetylglucosamine/N-acetylgalactosamine, hydroxyasparagine, serine, urea, 1-methylnicotinamide, fructose, 3-methylhistidine, pimelate, 4-acetylphenol sulfate, N-acetyltryptophan, stachydrine, felinine, N4-acetylcytidine, 2-methylmalonylcarnitine, 4-vinylphenol sulfate, dimethylarginine (SDMA+ADMA), N2,N2-dimethylguanine, N6-methyllysine, equol sulfate, prolylglycine, O-sulfo-L-tyrosine, N6,N6-dimethyllysine, dihydrocaffeate sulfate (2), 2,6-dihydroxybenzoic acid, picolinoylglycine, vanillic acid, glycine, guanosine, N-acetylalanine, urate, azelate, arginine, nicotinamide, ornithine, orotate, transurocanate, N-acetylglutamate, ribitol, indolelactate, maleate, cysteine s-sulfate, 1-methylhistamine, 4-hydroxyhippurate, isovalerylglycine, 7-methylguanine, N6-acetyllysine, pyrraline, N6-carboxymethyllysine, cyclo (gly-pro), 2-hydroxyglutarate, N-acetyl-cadaverine, felinylglycine, 2-piperidinone, 3-acetylphenol sulfate, methionine sulfone, fructosyllysine, 4-vinylguaiacol sulfate, 4-methoxyphenol sulfate, daidzein sulfate (2), 3-methoxycatechol sulfate (2), N-acetylkynurenine (2), arabitol/xylitol, indoleacetylglycine, 3-amino piperidone, 5-hydroxy-2-methylpyridine sulfate, 4-vinylcatechol sulfate, oxindolylalanine, N1-methyladenosine, choline, 3-phosphoglycerate, N('1)-acetyl spermidine, ethylmalonate, guanidinoacetate, and allantoin.

Additional features and advantages are described herein and will be apparent from the following Detailed Description

DETAILED DESCRIPTION

Definitions

As used in this disclosure and the appended claims, the singular forms "a," "an" and "the" include plural referents unless the context clearly dictates otherwise. Thus, for example, reference to "a composition" or "the composition" includes two or more compositions. The term "and/or" used in the context of "X and/or Y" should be interpreted as "X," or "Y," or "X and Y." Where used herein, the terms "example" and "such as," particularly when followed by a listing of terms, are merely exemplary and illustrative, and are not exclusive or comprehensive.

As used herein, "about" is understood to refer to numbers in a range of numerals, for example the range of −10% to +10% of the referenced number, within −5% to +5% of the referenced number, or in one aspect, within −1% to +1% of the referenced number, and in a specific aspect, within −0.1% to +0.1% of the referenced number. Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

All percentages expressed herein are by weight of the composition on a dry matter basis unless specifically stated otherwise. The skilled artisan will appreciate that the term "dry matter basis" means that an ingredient's concentration or percentage in a composition is measured or determined after any free moisture in the composition has been removed. When reference is made to the pH, values correspond to pH measured at 25° C. with standard equipment. An "amount" can be the total amount of the referenced component per serving of the composition or per distinct unit of the composition and/or can be the weight percentage of the referenced component by dry weight. Moreover, an "amount" includes zero; for example, the recitation of an amount of a compound does not necessarily mean that the compound is present, unless followed by a range that excludes zero.

The terms "food," "food product" and "food composition" mean a product or composition that is intended for ingestion by an animal and provides at least one nutrient to the animal. Further in this regard, these terms mean that the product or composition is in a form ready for consumption and is not merely an intermediate from which a consumable product or composition is made, although other food compositions can be added in some embodiments. The term "pet food" means any food composition intended to be consumed by a pet. The term "pet" means any animal which could benefit from or enjoy the compositions provided by the present disclosure. For example, the pet can be an avian, bovine, canine, equine, feline, hircine, lupine, murine, ovine, or porcine animal, but the pet can be any suitable animal.

The term "complete and balanced" when referring to a food composition means a food composition that contains all known required nutrients in appropriate amounts and proportions based on recommendations of recognized authorities in the field of animal nutrition, and are therefore capable of serving as a sole source of dietary intake to maintain life or promote production, without the addition of supplemental nutritional sources. Nutritionally balanced pet food and animal food compositions are widely known and widely used in the art, e.g., complete and balanced food compositions formulated according to standards established by the Association of American Feed Control Officials (AAFCO) as of Jan. 1, 2021.

The term "companion animal" means a dog or a cat. In an embodiment, the compositions and methods disclosed herein involve a senior cat.

As used herein, "chronic kidney disease" or "CKD" is defined as the presence of structural or functional abnormalities of one or both kidneys that have been present for 3 months or longer. In one embodiment, the CKD can be diagnosed as one of 4 stages as defined by the International Renal Interest Society (IRIS) guidelines (modified 2019) (http://www.iris-kidney.com/guidelines/staging.html).

As used herein, "early-stage chronic kidney disease" or "early-stage CKD" refers to stage 1 and/or stage 2 of chronic kidney disease.

As used herein, "late-stage chronic kidney disease" or "late-stage CKD" refers to stage 3 and/or stage 4 of chronic kidney disease.

As used herein, "normalized relative abundance" refers to the area-under-the-curve of ion counts of each biomarker, as measured by liquid chromatography and mass spectrometry, further transformed using logarithm base 2 and auto-scaled to achieve a zero mean and unit variance. Such measurements are known in the art and have been described by Metabolon Inc. For example, details and further information are found in Ford et al. Appl Lab Med 2020 and Li et al. J Am Heart Assoc 2021.

The term "B vitamin" refers to any B vitamin including derivatives, acidic forms, and salts thereof. Such B vitamins can include without limitation, vitamin B1 (thiamine), vitamin B2 (riboflavin), vitamin B3 (niacin, nicotinic acid, nicotinamide), vitamin B5 (pantothenic acid), vitamin B6 (pyridoxine, pyridoxal, pyridoxamine), vitamin B7 (biotin), vitamin B8 (myo-inositol), vitamin B9 (folic acid) vitamin B12 (cobalamin compounds including methylcobalamin, hydroxocobalamin, and cyanocobalamin).

"Wet food" means a pet food having a moisture content from about 50% to about 90%, and in one aspect, from about 70% to about 90%. "Dry food" means a pet food having a moisture content less than about 20%, and in one aspect, less than about 15%, and in a specific aspect, less than about 10%. "Semi-moist food" means a pet food having a moisture content from about 20% to about 50%, and in one aspect, from about 25% to about 35%.

"Kibbles" is used synonymously with "chunks" herein and both terms mean pieces of dry or semi-moist pet food which can have a pellet shape or any other shape and can be made by slicing a food composition into separate pieces. Non-limiting examples of kibbles include particulates; pellets; pieces of pet food, dehydrated meat, meat analog, vegetables, and combinations thereof; and pet snacks, such as meat or vegetable jerky, rawhide, and biscuits. A "meat analog" is a meat emulsion product that resembles pieces of natural meat in appearance, texture, and physical structure.

The term "effective amount" or "therapeutically effect amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In some aspects, the particular disease, condition, or disorder can be chronic kidney disease.

The term "dietary supplement" means a product that is intended to be ingested in addition to the normal animal diet. Dietary supplements may be in any form, e.g., solid, liquid, gel, tablets, capsules, powder, and the like. In one aspect, they can be provided in convenient dosage forms. In some embodiments, they can be provided in bulk consumer packages such as bulk powders, liquids, gels, or oils. In other embodiments, supplements can be provided in bulk quantities to be included in other food items such as snacks, treats, supplement bars, beverages and the like.

The term "long-term administration" means periods of repeated administration or consumption in excess of one month. Periods of longer than two, three, or four months can be used for certain embodiments. Also, more extended periods can be used that include longer than 5, 6, 7, 8, 9, or 10 months. Periods in excess of 11 months or 1 year can also be used. Longer term use extending over 1, 2, 3, or more years are included in the invention. For certain aging animals, the animal will continue consuming on a regular basis for the remainder of its life. This can also be referred to as consumption for "extended" periods.

The term "regular basis" means at least monthly dosing with the compositions or consumption of the compositions, and in one aspect, means at least weekly dosing. More frequent dosing or consumption, such as twice or three times weekly, can be performed in certain embodiments. Still, in other embodiments, regimens can be used that comprise at least once daily consumption.

The compositions disclosed herein may lack any element that is not specifically disclosed herein. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified. Any embodiment disclosed herein can be combined with any other embodiment disclosed herein unless explicitly and directly stated otherwise.

Unless defined otherwise, all technical and scientific terms and any acronyms used herein have the same meanings as commonly understood by one of ordinary skill in the art in the field of the invention. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof, are relevant prior art for the present invention and the right to challenge the accuracy and pertinence of such patents, patent applications, publications, and other references is specifically reserved.

Embodiments

In one embodiment, a method of diagnosing chronic kidney disease (CKD) in a feline can comprise measuring a normalized relative abundance of a first urine biomarker selected from the urine biomarkers listed in Table 1 or Table 2 as described in Example 1. The method can further comprise determining that the feline has CKD if the normalized relative abundance of the first urine biomarker has a value outside the range under the non-CKD column, determining that the feline has early-stage chronic kidney disease if the normalized relative abundance of the first urine biomarker has a value in the range under the early-stage CKD column, or determining that the feline has late-stage CKD if the normalized relative abundance of the first urine biomarker has a value in the range under the late-stage CKD column.

Additionally, a method of enabling treatment or slowing progression of chronic kidney disease in a feline can comprise diagnosing CKD in the feline as discussed herein and recommending a composition for the feline, wherein the composition treats or slows the progression of CKD in the feline.

Further, a feline urine biomarker for diagnosing early-stage CKD in a feline can be selected from the group consisting of sulfate, N-acetylglucosamine/N-acetylgalactosamine, hydroxyasparagine, serine, urea, 1-methylnicotinamide, fructose, 3-methylhistidine, pimelate, 4-acetylphenol sulfate, N-acetyltryptophan, stachydrine, felinine, N4-acetylcytidine, 2-methylmalonylcarnitine, 4-vinylphenol sulfate, dimethylarginine (SDMA+ADMA), N2,N2-dimethylguanine, N6-methyllysine, equol sulfate, prolylglycine, O-sulfo-L-tyrosine, N6,N6-dimethyllysine, dihydrocaffeate sulfate (2), 2,6-dihydroxybenzoic acid, picolinoylglycine, vanillic acid, glycine, guanosine, N-acetylalanine, urate, azelate, arginine, nicotinamide, ornithine, orotate, trans-urocanate, N-acetylglutamate, ribitol, indolelactate, maleate, cysteine s-sulfate, 1-methylhistamine, 4-hydroxyhippurate, isovalerylglycine, 7-methylguanine, N6-acetyllysine, pyrraline, N6-carboxymethyllysine, cyclo(gly-pro), 2-hydroxyglutarate, N-acetyl-cadaverine, felinylglycine, 2-piperidinone, 3-acetylphenol sulfate, methionine sulfone, fructosyllysine, 4-vinylguaiacol sulfate, 4-methoxyphenol sulfate, daidzein sulfate (2), 3-methoxycatechol sulfate (2), N-acetylkynurenine (2), arabitol/xylitol, indoleacetylglycine, 3-amino-2-piperidone, 5-hydroxy-2-methylpyridine sulfate, 4-vinylcatechol sulfate, oxindolylalanine, N1-methyladenosine, choline, 3-phosphoglycerate, N('1)-acetyl spermidine, ethylmalonate, guanidinoacetate, and allantoin.

Generally, the present methods of diagnosing a feline with CKD involve measuring the relative abundance of a urine biomarker and determining that the feline has CKD, including in some aspects, whether the feline has early-stage or late-stage CKD, based on specific ranges as disclosed herein. Such diagnosis is possible based on the novel biomarkers and ranges discovered by the present inventors.

While the present markers have unique ranges allowing for diagnosis between early-stage and late-stage CKD, some markers have an indeterminate range where the specific stage is not conclusive. As such, the present methods include the use of multiple markers to allow a diagnosis between early-stage and late-stage CKD. As such, in one embodiment, the method can further comprise measuring a normalized relative abundance of a second urine biomarker when the normalized relative abundance of the first urine biomarker has a value in the range under the indeterminate stage column, and further determining that the feline has early-stage chronic kidney disease if the normalized relative abundance of the second urine biomarker has a value in the range under the early-stage CKD column, or determining that the feline has late-stage CKD if the normalized relative abundance of the second urine biomarker has a value in the range under the late-stage CKD column.

Additionally, the method can further comprise measuring a normalized relative abundance of a third urine biomarker when the normalized relative abundances of the first and second urine biomarkers have values in the range under the indeterminate stage column, and further determining that the feline has early-stage chronic kidney disease if the normalized relative abundance of the third urine biomarker has a value in the range under the early-stage CKD column, or determining that the feline has late-stage CKD if the normalized relative abundance of the third urine biomarker has a value in the range under the late-stage CKD column.

Further, the method can further comprise measuring a normalized relative abundance of a fourth urine biomarker when the normalized relative abundances of the first, second, and third urine biomarkers have values in the range under the indeterminate stage column, and further determining that the feline has early-stage chronic kidney disease if the normalized relative abundance of the fourth urine biomarker has a value in the range under the early-stage CKD column, or determining that the feline has late-stage CKD if the normalized relative abundance of the fourth urine biomarker has a value in the range under the late-stage CKD column. Other markers can also be measured in like manner, e.g., a fifth marker, sixth marker, seventh marker, etc.

As such, the present step of determining can be based on one marker, two markers, three markers, four markers, five markers, six markers, seven markers, eight markers, nine markers, ten markers, and so on. When multiple markers are used, the diagnosis between early-stage and late-stage can be based on a simple majority if the markers indicate more than one stage, e.g., if seven markers are used and five of the seven indicate early-stage and two of the seven indicate late-stage, a diagnosis of early-stage can be made.

Generally, a method of enabling treatment, treating, or slowing progression of chronic kidney disease in a feline can comprise diagnosing chronic kidney disease (CKD) in the feline as discussed herein and recommending or providing a composition for the feline, wherein the composition treats or slows the progression of CKD in the feline.

Such compositions can be any composition that is beneficial for providing nutrition to felines having CKD. In one embodiment, the composition can include a combination of glycine, methionine, cysteine, and glutamine. In one aspect, the amino acid blend of glycine, methionine, cysteine, and glutamine can be synergistic for treating renal cats. In another aspect, the amino acid blend can be free form amino acids. In still another aspect, the amino acid blend can further comprise at least one of protein, carbohydrates, fat, and fiber. In one embodiment, the composition can comprise medium chain triglycerides. In another embodiment, the composition can contain less than 1% of phosphorous compounds and/or phosphate compounds. In still another embodiment, the composition can contain less than 1% of potassium. In yet another embodiment, the composition can have protein and phosphorus in a ratio between 5:1 and 15:1. In one embodiment, the composition can comprise arginine, eicosapentaenoic acid, docosahexaenoic acid, vitamin E, and B vitamins. Such B vitamins can include any combination of vitamin B1 (thiamine), vitamin B2 (riboflavin), vitamin B3 (niacin, nicotinic acid, nicotinamide), vitamin B5 (pantothenic acid), vitamin B6 (pyridoxine, pyridoxal, pyridoxamine), vitamin B7 (biotin), vitamin B8 (myo-inositol), vitamin B9 (folic acid) vitamin B12 (cobalamin compounds including methylcobalamin, hydroxocobalamin, and cyanocobalamin).

Generally, the composition can be administered sufficiently such that the treatment is effective. In one aspect, the administration can be on a regular basis. In another aspect, the administration can be a long-term administration. Administration of the composition can include any manner of delivery. In one embodiment, the composition can be administered in conjunction with a pet food composition. In another embodiment, the composition is a pet food. In still another embodiment, the composition can be a sachet or supplement administered in conjunction with a pet food. In yet another embodiment, the composition can be a sachet or supplement administered separately from other food compositions.

Generally, the protein can be any crude protein material and may comprise vegetable proteins such as soybean meal, soy protein concentrate, corn gluten meal, wheat gluten, cottonseed, pea protein, canola meal, and peanut meal, or animal proteins such as casein, albumin, and meat protein. Examples of meat protein useful herein include beef, pork, lamb, equine, poultry, fish, and mixtures thereof. The compositions may also optionally comprise other materials such as whey and other dairy by-products. In one aspect, the protein comprises collagen, whey, or a mixture thereof. In one embodiment, the food compositions can comprise protein in amounts from about 10%, 20%, 30%, 35%, 40%, 45%, 50%, or even 55% to about 20%, 25%, 30%, 35%, 40%, 45%, 50%, 55%, 60%, or even 70% by weight, including various subranges within these amounts. In one aspect, the protein can be from about 20% to about 60% of the food composition by weight. In another aspect, the protein can be from about 25% to about 50% of the food composition by weight.

Additionally, the present compositions can comprise isoflavones. In various embodiments, the isoflavones include at least one of daidzein, 6-O-malonyl daidzein, 6-O-acetyl daidzein, genistein, 6-O-malonyl genistein, 6-O-acetyl genistein, glycitein, 6-O-malonyl glycitein, 6-O-acetyl glycitein, biochanin A, or formononetin. The isoflavones or metabolites thereof can be from soybean (Glycine max) in certain embodiments. Where present, the one or more metabolites preferably include equol. In one embodiment, the food compositions can comprise isoflavones in amounts from about 300, 400, 500, 600, 700, 800, 900, or even 1,000 mg per kg of the food composition to about 500; 600; 700; 800; 900; 1,000; 1,100; 1,200; 1,300; 1,400; or even 1,500 mg per kg of the food composition, including various subranges within these amounts. In one aspect, the isoflavones can present in an amount from about 300 mg to 1,500 mg per kilogram of the pet food composition. In another aspect, the isoflavones can present in an amount from about 700 mg to 1,200 mg per kilogram of the pet food composition.

Generally, any type of carbohydrate can be used in the food compositions. Examples of suitable carbohydrates include grains or cereals such as rice, corn, millet, sorghum, alfalfa, barley, soybeans, canola, oats, wheat, rye, triticale and mixtures thereof. In one embodiment, the carbohydrate comprises from about 10% to about 70% of the food composition by weight. In another embodiment, the carbohydrate comprises from about 20% to about 60% of the food compositions by weight. In other aspects, the carbohydrate can be present in amounts from about 10%, 20%, 30%, 40%, or even 50%, to about 20%, 30%, 40%, 50%, 60%, or even 70% by weight.

Generally, the food compositions include fat. Examples of suitable fats include animal fats and vegetable fats. In one aspect, the fat source can be an animal fat source such as tallow, lard, or poultry fat. Vegetable oils such as corn oil, sunflower oil, safflower oil, grape seed oil, soybean oil, olive oil, fish oil and other oils rich in monounsaturated and n-6 and n-3 polyunsaturated fatty acids, may also be used. In one embodiment, the food compositions can comprise fat in amounts from about 5%, 10%, 15%, 20%, 25%, 30%, 35%, 40%, 45%, or even 50% to about 15%, 20%, 25%, 30%, 35%, 40%, 45%, 50%, 55%, or even 60%, including various subranges within these amounts by weight. In one aspect, the fat comprises from about 10% to about 40% of the food composition by weight. In another aspect, the fat comprises from about 20% to about 35% of the food composition by weight.

Additionally, the present compositions can comprise omega-3 fatty acids. Non-limiting examples of suitable omega-3 fatty acids include eicosapentaenoic acid (EPA), docosahexaenoic acid (DHA), alpha-linolenic acid (ALA) and mixtures thereof. In one embodiment, the omega-3 fatty acids can range from about 0.2%, 0.5%, 1%, 2%, or even 3% to about 1%, 2%, 3%, 4%, or even 5% of the composition by weight. In some embodiments, the omega-3 fatty acids are present in the food composition in an amount from about 1% to about 5% by weight. In some embodiments, the omega-3 fatty acids are present in the food composition in an amount from about 1% to about 2% by weight.

In addition to the fats and fatty acids discussed herein, the present compositions can comprise omega-6 fatty acids. Non-limiting examples of suitable omega-6 fatty acids include linoleic acid (LA), gamma-linolenic acid (GLA), arachidonic acid (AA, ARA), eicosadienoic acid, docosadienoic acid, and mixtures thereof. In one embodiment, the omega-6 fatty acids can range from about 0.2%, 0.5%, 1%, 2%, or even 3% to about 1%, 2%, 3%, 4%, or even 5% of the composition by weight. In some embodiments, the omega-6 fatty acids are present in the food composition in an amount from about 1% to about 5% by weight. In some embodiments, the omega-6 fatty acids are present in the food composition in an amount from about 1% to about 2% by weight.

The administration of the pet food compositions can be performed on as-needed basis, an as-desired basis, a regular basis, or intermittent basis. In one aspect, the food composition can be administered to the animal on a regular basis. In one aspect, at least weekly administration can be performed. More frequent administration or consumption, such as twice or three times weekly, can be performed in certain embodiments. In one aspect, an administration regimen can comprise at least once daily consumption.

According to the presently described methods, administration, including administration as part of a dietary regimen, can span a period ranging from parturition through the adult life of the animal. In certain embodiments, the animal can be a young or growing animal. In other embodiments, administration can begin, for example, on a regular or extended regular basis, when the animal has reached more than about 10%, 20%, 30%, 40%, or 50% of its projected or anticipated lifespan. In some embodiments, the animal can have attained 40, 45, or 50% of its anticipated lifespan. In yet other embodiments, the animal can be older having reached 60, 66, 70, 75, or 80% of its likely lifespan. A determination of lifespan may be based on actuarial tables, calculations, estimates, or the like, and may consider past, present, and future influences or factors that are known to positively or negatively affect lifespan. Consideration of species, gender, size, genetic factors, environmental factors and stressors, present and past health status, past and present nutritional status, stressors, and the like may also influence or be taken into consideration when determining lifespan.

Such administration can be performed for a time required to accomplish one or more objectives described herein, e.g., treating renal disease. Other administration amounts may be appropriate and can be determined based on the animal's initial weight as well as other variables such as species, gender, breed, age, desired health benefit, etc.

The moisture content for pet food compositions varies depending on the nature of the food composition. The food compositions may be dry compositions (e.g., kibble), semi-moist compositions, wet compositions, or any mixture thereof. In one embodiment, the composition can be a complete and nutritionally balanced pet food. In this embodiment, the pet food may be a "wet food", "dry food", or food of "intermediate moisture" content. "Wet food" describes pet food that is typically sold in cans or foil bags and has a moisture content typically in the range of about 70% to about 90%. "Dry food" describes pet food that is of a similar composition to wet food but contains a limited moisture content typically in the range of about 5% to about 15% or 20% (typically in the form or small biscuit-like kibbles). In one embodiment, the compositions can have moisture content from about 5% to about 20%. Dry food products include a variety of foods of various moisture contents, such that they are relatively shelf-stable and resistant to microbial or fungal deterioration or contamination. Also, in one aspect, dry food compositions can be extruded food products for companion animals.

The food compositions may also comprise one or more fiber sources. Such fiber sources include fiber that is soluble, insoluble, fermentable, and nonfermentable. Such fibers can be from plant sources such as marine plants, but microbial sources of fiber may also be used. A variety of soluble or insoluble fibers may be utilized, as will be known to those of ordinary skill in the art. The fiber source can be beet pulp (from sugar beet), gum arabic, gum talha, psyllium, rice bran, corn bran, wheat bran, oat bran, carob bean gum, citrus pulp, pectin, fructooligosaccharide, short chain oligofructose, mannanoligofructose, soy fiber, arabinogalactan, galactooligosaccharide, arabinoxylan, cellulose, chicory, or mixtures thereof.

Alternatively, the fiber source can be a fermentable fiber. Fermentable fiber has previously been described to provide a benefit to the immune system of a companion animal. Fermentable fiber or other compositions known to skilled artisans that provide a prebiotic to enhance the growth of probiotics within the intestine may also be incorporated into the composition to aid in the enhancement of the benefits described herein or to the immune system of an animal.

In one embodiment, the food compositions can include a total dietary fiber from about 1% to about 15% by weight. In some aspects, the total dietary fiber can be included in an amount from about 5% to about 15% by weight, or even from about 8% to about 13% by weight. In another embodiment, the food compositions can include crude fiber from about 1% to about 10% by weight. In some aspects, the crude fiber can be included in an amount from about 3% to about 10% by weight, or even from about 3% to about 7% by weight.

In some embodiments, the ash content of the food composition ranges from less than 1% to about 15%. In one aspect, the ash content can be from about 5% to about 10%.

Generally, the food composition can be a meal, component of a meal, a snack, supplement, or a treat. Such compositions can include complete foods intended to supply the necessary dietary requirements for an animal.

Pet food compositions may further comprise one or more substances such as vitamins, minerals, antioxidants, probiotics, prebiotics, salts, and functional additives such as palatants, colorants, emulsifiers, and antimicrobial or other preservatives. Non-limiting examples of suitable preservatives include potassium sorbate, sorbic acid, sodium methyl para-hydroxybenzoate, calcium propionate, propionic acid, and combinations thereof. Minerals that may be useful in such compositions include, for example, calcium, phosphorous, potassium, sodium, iron, chloride, boron, copper, zinc, magnesium, manganese, iodine, selenium, and the like. Examples of additional vitamins useful herein include such fat-soluble vitamins as A, D, E, and K and water-soluble vitamins including B vitamins, and vitamin C. Inulin, amino acids, enzymes, coenzymes, and the like may be useful to include in various embodiments.

Specific amounts for each additional ingredient in the pet food compositions disclosed herein will depend on a variety of factors such as the ingredient included in the first edible material and any second edible material; the species of animal; the animal's age, body weight, general health, sex, and diet; the animal's consumption rate; the purpose for which the food product is administered to the animal; and the like. Therefore, the components and their amounts may vary widely.

For example, the amount of any of the above-noted ingredients can be decreased or increased based on the estimated effect on CKD in a feline.

EXAMPLES

The following non-limiting examples are illustrative of embodiments of the present disclosure.

Example 1—CKD Study of Felines

Urine samples from 25 health cats and 25 cats with different stages of CKD, including four stage 1 cats, sixteen stage 2 cats, four stage 3 cats, and one stage 4 cat, were collected for untargeted metabolomics analysis. The stages were diagnosed per the International Renal Interest Society (IRIS) guidelines (modified 2019) (http://www.iris-kidney-.com/guidelines/staging.html).

Metabolites with different concentrations between healthy cats and cats with CKD were identified. The effects of sex and age were adjusted. The metabolite biomarker signatures were selected based on the combination of following criteria:

1. Student's t tests with pooled variance were performed to compare healthy cats, cats with early-stage CKD. P values were adjusted for multiple testing errors. Metabolites with adjusted p values less than 0.05 and fold change greater than 1.5 between cats with early-stage CKD and healthy cats were selected.

2. For each metabolite, the area under the curve (AUC) value of the receiver operating characteristic (ROC) curve, which indicates accuracy for classification, was calculated between healthy cats and cats with CKD. Metabolites with the AUC value greater than or equal to 0.8 were selected.

3. Random Forest machine learning was performed to identify metabolites that are discriminative between healthy vs. CKD cats. Metabolites with the mean decrease accuracy score greater than 0.001 were selected.

4. Intersect of the three groups of metabolites from steps 1-3 above.

Normalized relative abundance was calculated for the urine metabolites with differentiation of CKD cats versus healthy cats as shown in Table 1.

TABLE 1

| | Diagnostic Range (measured as normalized relative abundance) | | | |
|---|---|---|---|---|
| Urine Biomarker | Late-Stage CKD | Indeterminate Stage | Early-Stage Stage | Non-CKD |
| Sulfate | <−1.32 | −1.319 to −0.58 | −0.579 to 0.20 | >0.21 |
| N-acetylglucosamine/N-acetylgalactosamine | <−1.41 | −1.4 to −0.61 | −0.60 to 0.20 | >0.21 |
| hydroxyasparagine | <−1.29 | −1.28 to −0.55 | −0.54 to 0.40 | >0.41 |
| serine | <−1.32 | −1.31 to −0.74 | −0.739 to 0.40 | >0.41 |
| urea | <−1.32 | −1.31 to −0.73 | −0.72 to 0.30 | >0.31 |
| 1-methylnicotinamide | <−1.04 | −1.03 to −0.71 | −0.72 to 0.40 | >0.41 |
| fructose | <−1.06 | −1.05 to −0.75 | −0.74 to 0.40 | >0.41 |
| 3-methylhistidine | — | — | −0.77 to 0.50 | >0.51 |
| pimelate | <−1.3 | −1.29 to −0.64 | −0.63 to 0.20 | >0.21 |
| 4-acetylphenol sulfate | <−1.1 | −1.09 to −0.68 | −0.67 to 0.30 | >0.31 |
| N-acetyltryptophan | <−1.07 | −1.06 to −0.75 | −0.74 to 0.1 | >0.11 |
| stachydrine | <−1.5 | −1.4 to −0.88 | −0.87 to 0.30 | >0.31 |
| felinine | <−1.4 | −1.39 to −0.64 | −0.63 to 0.35 | >0.36 |
| N4-acetylcytidine | <−0.92 | −0.91 to 0.00 | 0.01 to 0.30 | >0.31 |
| 2-methylmalonylcarnitine | <−0.57 | −0.56 to −0.38 | −0.37 to 0.32 | >0.33 |
| 4-vinylphenol sulfate | <−1.35 | −1.34 to −0.60 | −0.59 to 0.40 | >0.41 |
| dimethylarginine (SDMA + ADMA) | <−1.2 | −1.1 to −0.74 | −0.73 to 0.43 | >0.44 |
| N2,N2-dimethylguanine | <−1.1 | −1.1 to −0.65 | −0.64 to 0.40 | >0.41 |
| N6-methyllysine | <−1.4 | −1.3 to −0.62 | −0.61 to 0.20 | >0.21 |
| equol sulfate | — | — | −0.72 to 0.30 | >0.31 |
| prolylglycine | <−1.2 | −1.1 to −0.85 | −0.84 to 0.20 | >0.21 |
| O-sulfo-L-tyrosine | <−1.5 | −1.4 to −0.56 | −0.55 to 0.50 | >0.51 |
| N6,N6-dimethyllysine | <−1.24 | −1.23 to −1.17 | −1.16 to 0.30 | >0.31 |
| dihydrocaffeate sulfate (2) | <−0.89 | −0.88 to −0.60 | −0.59 to −0.36 | >0.361 |
| 2,6-dihydroxybenzoic acid | <−0.86 | −0.85 to −0.63 | −0.62 to 0.25 | >0.26 |
| picolinoylglycine | <−1.1 | −1.0 to −0.79 | −0.78 to 0.20 | >0.21 |
| vanillic acid glycine | <−0.77 | −0.76 to −0.63 | −0.62 to 0.20 | >0.21 |
| guanosine | <−1.1 | −1.0 to −0.55 | −0.54 to 0.43 | >0.431 |
| N-acetylalanine | <−1.22 | −1.21 to −0.54 | −0.53 to 0.0 | >0.1 |
| urate | <−1.34 | −1.33 to −0.58 | −0.57 to 0.40 | >0.41 |
| azelate | <−1.24 | −1.23 to −0.91 | −0.90 to 0.0 | >0.01 |
| arginine | <−1.34 | −1.33 to −0.72 | −0.71 to 0.49 | >0.50 |
| nicotinamide | <−1.4 | −1.3 to −0.74 | −0.73 to 0.20 | >0.21 |
| ornithine | <−1.32 | −1.31 to −1.0 | −0.99 to 0.30 | >0.31 |
| orotate | <−1.53 | −1.52 to −0.50 | −0.49 to 0.32 | >0.33 |
| trans-urocanate | <−1.44 | −1.43 to −0.78 | −0.77 to 0.35 | >0.36 |
| N-acetylglutamate | <−1.2 | −1.1 to −0.87 | −0.86 to 0.30 | >0.31 |
| ribitol | <−1.39 | −1.38 to −0.27 | −0.26 to 0.40 | >0.41 |
| indolelactate | <−1.13 | −1.12 to −0.81 | −0.80 to 0.20 | >0.21 |
| maleate | <−1.0 | — | −0.99 to 0.10 | >0.11 |
| cysteine s-sulfate | <−0.88 | −0.87 to −0.18 | −0.17 to 0.10 | >0.11 |
| 1-methylhistamine | <−0.79 | −0.78 to −0.16 | −0.15 to 0.33 | >0.34 |
| 4-hydroxyhippurate | <−1.23 | −1.22 to −0.90 | −0.89 to 0.10 | >0.11 |
| isovalerylglycine | <−1.2 | −1.1 to −0.94 | −0.93 to 0.20 | >0.21 |
| 7-methylguanine | <−1.3 | −1.2 to −0.56 | −0.55 to 0.30 | >0.31 |
| N6-acetyllysine | <−1.3 | −1.2 to −0.60 | −0.59 to 0.24 | >0.25 |
| pyrraline | <−0.49 | −0.48 to −0.36 | −0.35 to 0.20 | >0.21 |

TABLE 1-continued

| Urine Biomarker | Diagnostic Range (measured as normalized relative abundance) | | | |
| --- | --- | --- | --- | --- |
| | Late-Stage CKD | Indeterminate Stage | Early-Stage Stage | Non-CKD |
| N6-carboxymethyllysine | <−1.2 | −1.1 to −0.83 | −0.82 to 0.30 | >0.31 |
| cyclo(gly-pro) | <−1.17 | — | −1.16 to 0.35 | >0.36 |
| 2-hydroxyglutarate | <−1.21 | −1.20 to −0.91 | −0.90 to 0.0 | >0.1 |
| N-acetyl-cadaverine | <−1.3 | −1.2 to −0.31 | −0.30 to 0.34 | >0.35 |
| felinylglycine | <−1.1 | −1.0 to −0.91 | −0.90 to 0.10 | >0.11 |
| 2-piperidinone | <−1.1 | −1.0 to −0.66 | −0.65 to 0.17 | >0.18 |
| 3-acetylphenol sulfate | <−1.03 | −1.02 to −1.01 | −1.0 to 0.20 | >0.21 |
| methionine sulfone | <−0.72 | −0.71 to −0.20 | −0.19 to 0.35 | >0.36 |
| fructosyllysine | <−1.0 | −0.99 to −0.86 | −0.85 to 0.30 | >0.31 |
| 4-vinylguaiacol sulfate | <−1.4 | −1.3 to −0.60 | −0.59 to 0.40 | >0.41 |
| 4-methoxyphenol sulfate | — | — | 0.61 to 0.45 | >0.451 |
| daidzein sulfate (2) | — | — | −0.82 to 0.30 | >0.31 |
| 3-methoxycatechol sulfate (2) | <−1.15 | −1.14 to −0.67 | −0.66 to 0.50 | >0.51 |
| N-acetylkynurenine (2) | <−1.1 | −1.0 to −0.62 | −0.61 to 0.10 | >0.11 |
| arabitol/xylitol | <−1.35 | −1.34 to −0.75 | −0.74 to 0.30 | >0.31 |
| indoleacetylglycine | <−1.2 | −1.1 to −0.55 | −0.54 to 0.24 | >0.25 |
| 3-amino-2-piperidone | <−1.4 | −1.3 to −1.2 | −1.1 to 0.30 | >0.31 |
| 5-hydroxy-2-methylpyridine sulfate | <−1.1 | −1.0 to −0.47 | −0.46 to 0.02 | >0.03 |
| 4-vinylcatechol sulfate | <−1.0 | −0.99 to −0.60 | −0.59 to 0.40 | >0.41 |
| oxindolylalanine | <−1.0 | — | −0.99 to 0.10 | >0.11 |
| N1-methyladenosine | <−1.21 | −1.20 to −0.49 | −0.48 to 0.35 | >0.36 |
| choline | <−1.0 | −0.99 to −0.86 | −0.85 to 0.20 | >0.21 |
| 3-phosphoglycerate | <−0.96 | −0.95 to −0.83 | −0.82 to 0.40 | >0.41 |
| N('1)-acetylspermidine | <−1.1 | −1.0 to −0.82 | −0.81 to 0.39 | >0.40 |
| ethylmalonate | <−1.15 | −1.14 to −0.66 | −0.65 to 0.30 | >0.31 |
| guanidinoacetate | <−1.39 | −1.38 to −0.87 | −0.86 to 0.65 | >0.64 |
| allantoin | <−1.34 | −1.33 to −0.68 | −0.67 to 0.36 | >0.37 |

In one embodiment, the urine markers can be selected from the group consisting of sulfate, N-acetylglucosamine/N-acetylgalactosamine, hydroxyasparagine, serine, urea, 1-methylnicotinamide, and fructose. In another embodiment, the urine markers can be selected from the group consisting of sulfate, N-acetylglucosamine/N-acetylgalactosamine, hydroxyasparagine, serine, urea, 1-methylnicotinamide, fructose, 3-methylhistidine, pimelate, 4-acetylphenol sulfate, N-acetyltryptophan, stachydrine, felinine, N4-acetylcytidine, 2-methylmalonylcarnitine, 4-vinylphenol sulfate, dimethylarginine (SDMA+ADMA), N2,N2-dimethylguanine, N6-methyllysine, equol sulfate, prolylglycine, O-sulfo-L-tyrosine, N6,N6-dimethyllysine, dihydrocaffeate sulfate (2), 2,6-dihydroxybenzoic acid, picolinoylglycine, vanillic acid, glycine, guanosine, N-acetylalanine, urate, azelate, arginine, nicotinamide, ornithine, orotate, and trans-urocanate. In one aspect, the method can include using felinine as a biomarker. In another aspect, the method can include using allantoin as a biomarker.

Other markers that can be used to diagnose CKD include N-(2-furoyl)glycine, allo-threonine, 1,2,3-benzenetriol sulfate (2), 2-oxoarginine, 4-hydroxycinnamate sulfate, 3-hydroxy-2-methylpyridine sulfate, 4-methylcatechol sulfate, pyridoxate, 4-ethylphenylsulfate, glycerate, dimethylmalonic acid, anthranilate, pantoate, furaneol sulfate, cysteine, 2-hydroxyhippurate (salicylurate), 3-hydroxypyridine sulfate, N,N-dimethylalanine, N-acetylmethionine sulfoxide, 2-oxindole-3-acetate, maltol sulfate, pyridoxal, adenosine, uridine, asparagine, lanthionine, 5-hydroxymethyl-2'-deoxycytidine, cholate, 1-ribosyl-imidazoleacetate, N-acetyl-glutamate, and pyridoxamine.

Based on the biomarkers in Table 1 (or Table 2 below), the present biomarkers can be used to diagnose CKD in cats as well as specific diagnosis of early-stage CKD and late-stage CKD. The method can include measuring a normalized relative abundance of the biomarker and determining that the feline has CKD if the normalized relative abundance of the marker is less than the range of the Non-CKD column according to Table 1. Additionally, further diagnosis can be made if the marker falls within the ranges of early-stage CKD or late-stage CKD. The method can also further comprise measuring additional markers to determine if the feline has early-stage or late-stage CKD according to the ranges listed in Table 1 when the first marker(s) fall within the ranges listed in the indeterminate stage.

Additional urine samples were collected from 30 privately-owned cats in London, UK: healthy cats (n=10), cats with stage 2 CKD (n=10), and cats with stage 3 CKD (n=10). Samples were frozen and stored in a −80° C. freezer until use. Details in sample collection, metabolomics assay, data processing and analysis were the same as previously described. Hydration and health status have a significant impact on urine concentration. Cats with CKD generally have a decreased urine specific gravity (USG) due to kidney's reduced capacity in concentrating urine. The USG value also changes with CKD progression. Thus, it is important to normalize urine samples by USG so that samples from different health states can be compared.

Studies showed urine osmolarity is a good estimator for USG. The urine metabolomics data were normalized to the osmolality of each sample on a per sample basis, trans- [5] formed using the logarithm to the base 2, and then auto-scaled to achieve a zero mean and unit variance for all metabolites. Statistical data analysis was performed as previously described.

The additional markers identified using the data set were summarized in Table 2.

TABLE 2

| Urine Biomarker | Diagnostic Range (measured as normalized relative abundance) | | | |
| --- | --- | --- | --- | --- |
| | Non-CKD | Early-Stage Stage | Indeterminate Stage | Late-Stage CKD |
| 1-methylguanidine | <0.72 | 0.72 to 1.41 | — | >1.41 |
| 4-ureidobutyrate | <0.77 | 0.77 to 1.38 | — | >1.38 |
| 1-methyl-5-imidazolelactate | <0.78 | 0.78 to 1.39 | — | >1.39 |
| scyllo-inositol | <0.79 | 0.79 to 1.28 | — | >1.28 |
| fucitol | <0.8 | 0.8 to 1.29 | — | >1.29 |
| N-acetyl-1-methylhistidine | <0.82 | 0.82 to 1.43 | — | >1.43 |
| arachidonate (20:4n6) | <0.83 | 0.83 to 1.47 | — | >1.47 |
| N-formylanthranilic acid | <0.83 | 0.83 to 1.36 | — | >1.36 |
| N-acetyl-isoputreanine | <0.85 | 0.85 to 1.34 | — | >1.34 |
| 3-methylglutarylcarnitine (2) | <0.86 | 0.86 to 1.35 | — | >1.35 |
| 2-O-methylascorbic acid | <0.87 | 0.87 to 1.42 | — | >1.42 |
| furaneol sulfate | <0.87 | 0.87 to 1.32 | — | >1.32 |
| glucuronate | <0.88 | 0.88 to 1.49 | — | >1.49 |
| citrate | <0.88 | 0.88 to 1.34 | — | >1.34 |
| benzoate | <0.88 | 0.88 to 1.31 | — | >1.31 |
| indolin-2-one | <0.88 | 0.88 to 1.28 | — | >1.28 |
| nicotinamide N-oxide | <0.89 | 0.89 to 1.47 | — | >1.47 |
| carboxyethyl-GABA | <0.9 | 0.9 to 1.44 | — | >1.44 |
| lyxonate | <0.9 | 0.9 to 1.34 | — | >1.34 |
| glucose | <0.9 | 0.9 to 1.69 | — | >1.69 |
| dimethylguanidino valeric acid (DMGV) | <0.91 | 0.91 to 1.43 | — | >1.43 |
| isocitrate | <0.91 | 0.91 to 1.42 | — | >1.42 |
| allantoic acid | <0.91 | 0.91 to 1.91 | — | >1.91 |
| 1-methyladenine | <0.92 | 0.92 to 1.46 | — | >1.46 |
| N-acetyltaurine | <0.92 | 0.92 to 1.44 | — | >1.44 |
| trimethylamine N-oxide | <0.92 | 0.92 to 1.41 | — | >1.41 |
| 4-hydroxyphenylacetoylcarnitine | <0.92 | 0.92 to 1.38 | — | >1.38 |
| 1-methylhypoxanthine | <0.92 | 0.92 to 1.34 | — | >1.34 |
| N-acetylneuraminate | <0.92 | 0.92 to 1.92 | — | >1.92 |
| malonylcarnitine | <0.93 | 0.93 to 1.5 | — | >1.5 |
| nicotinamide riboside | <0.93 | 0.93 to 1.47 | — | >1.47 |
| pimeloylcarnitine/3-methyladipoylcarnitine (C7-DC) | <0.93 | 0.93 to 1.35 | — | >1.35 |
| N-glycolylneuraminate | <0.93 | 0.93 to 1.6 | — | >1.6 |
| azelaoyltaurine | <0.93 | 0.93 to 1.89 | — | >1.89 |
| 3-carboxyadipate | <0.94 | 0.94 to 1.37 | — | >1.37 |
| dimethyl sulfone | <0.94 | 0.94 to 1.31 | — | >1.31 |
| tartronate (hydroxymalonate) | <0.95 | 0.95 to 1.44 | — | >1.44 |
| ascorbic acid 3-sulfate | <0.95 | 0.95 to 1.38 | — | >1.38 |
| malate | <0.95 | 0.95 to 1.35 | — | >1.35 |
| isovalerylcarnitine (C5) | <0.95 | 0.95 to 1.31 | — | >1.31 |
| glutarylcarnitine (C5-DC) | <0.96 | 0.96 to 1.64 | — | >1.64 |
| guanidinosuccinate | <0.97 | 0.97 to 1.41 | — | >1.41 |
| 3'-sialyllactose | <0.97 | 0.97 to 1.35 | — | >1.35 |
| 3-ureidopropionate | <0.97 | 0.97 to 1.68 | — | >1.68 |
| N6-succinyladenosine | <0.98 | 0.98 to 1.38 | — | >1.38 |
| C-glycosyltryptophan | <0.98 | 0.98 to 1.67 | — | >1.67 |
| isobutyrylcarnitine (C4) | <0.99 | 0.99 to 1.37 | — | >1.37 |
| N1-methylinosine | <0.99 | 0.99 to 1.63 | — | >1.63 |
| cysteinylglycine | <1.01 | 1.01 to 1.43 | — | >1.43 |
| 5,6-dihydrouridine | <1.01 | 1.01 to 1.84 | — | >1.84 |
| pseudouridine | <1.01 | 1.01 to 1.83 | — | >1.83 |
| 5-methylthioribose | <1.01 | 1.01 to 1.53 | — | >1.53 |
| 3,4-methylenevaleroylglycine | <1.02 | 1.02 to 1.42 | — | >1.42 |
| cysteine-glutathione disulfide | <1.02 | 1.02 to 1.52 | — | >1.52 |
| N-methylpipecolate | <1.03 | 1.03 to 1.43 | — | >1.43 |
| 7-methylurate | <1.03 | 1.03 to 1.32 | — | >1.32 |
| ribonate | <1.03 | 1.03 to 1.55 | — | >1.55 |
| N1-Methyl-2-pyridone-5-carboxamide | <1.04 | 1.04 to 1.66 | — | >1.66 |
| 1-methyl-4-imidazoleacetate | <1.05 | 1.05 to 1.56 | — | >1.56 |
| S-methylcysteine | <1.06 | 1.06 to 1.38 | — | >1.38 |
| creatinine | <1.07 | 1.07 to 2.03 | — | >2.03 |
| N-acetylserine | <1.1 | 1.1 to 1.54 | — | >1.54 |
| pyridoxate | <1.11 | 1.11 to 1.38 | — | >1.38 |

TABLE 2-continued

| Urine Biomarker | Non-CKD | Early-Stage Stage | Indeterminate Stage | Late-Stage CKD |
|---|---|---|---|---|
| | | Diagnostic Range (measured as normalized relative abundance) | | |
| gulonate | <1.11 | 1.11 to 1.47 | — | >1.47 |
| N-carbamoylputrescine | <1.14 | 1.14 to 1.65 | — | >1.65 |
| norvaline | <1.17 | 1.17 to 1.42 | — | >1.42 |
| tryptophan | >1.05 | 1.05 to 0.73 | — | <0.73 |
| phenyllactate (PLA) | >1.08 | 1.08 to 0.71 | — | <0.71 |
| dihydroorotate | >1.1 | 1.1 to 0.67 | — | <0.67 |
| N-acetylglycine | >1.11 | 1.11 to 0.64 | — | <0.64 |
| beta-guanidinopropanoate | >1.11 | 1.11 to 0.64 | — | <0.64 |
| 5-oxoproline | >1.12 | 1.12 to 0.62 | — | <0.62 |
| 5-hydroxylysine | >1.13 | 1.13 to 0.61 | — | <0.61 |
| cholate | >1.14 | 1.14 to 0.62 | — | <0.62 |
| azelate (C9-DC) | >1.16 | 1.16 to 0.61 | — | <0.61 |
| N-acetylvaline | >1.22 | 1.22 to 0.77 | — | <0.77 |
| glycylvaline | >1.23 | 1.23 to 0.77 | — | <0.77 |
| heptanoylglutamine | >1.23 | 1.23 to 0.76 | — | <0.76 |
| isovalerate (i5:0) | >1.26 | 1.26 to 0.75 | — | <0.75 |
| butyrylputrescine/isobutyrylputrescine | >1.28 | 1.28 to 0.77 | — | <0.77 |
| homoarginine | >1.28 | 1.28 to 0.77 | — | <0.77 |
| homostachydrine | >1.28 | 1.28 to 0.75 | — | <0.75 |
| N6-methyladenosine | >1.28 | 1.28 to 0.75 | — | <0.75 |
| 3-methoxytyramine | >1.29 | 1.29 to 0.91 | — | <0.91 |
| N-acetylhistamine | >1.29 | 1.29 to 0.79 | — | <0.79 |
| ferulylglycine (1) | >1.29 | 1.29 to 0.78 | — | <0.78 |
| S-methylcysteine sulfoxide | >1.3 | 1.3 to 0.84 | — | <0.84 |
| cyclo(pro-tyr) | >1.3 | 1.3 to 0.75 | — | <0.75 |
| N-lactoyl leucine | >1.31 | 1.31 to 0.74 | — | <0.74 |
| histamine | >1.31 | 1.31 to 0.72 | — | <0.72 |
| gamma-glutamylglycine | >1.31 | 1.31 to 0.73 | — | <0.73 |
| putrescine | >1.32 | 1.32 to 0.78 | — | <0.78 |
| alanyllysine | >1.32 | 1.32 to 0.74 | — | <0.74 |
| chenodeoxycholic acid sulfate (2) | >1.32 | 1.32 to 0.74 | — | <0.74 |
| N2,N2-dimethylguanosine | >1.33 | 1.33 to 0.77 | — | <0.77 |
| S-adenosylmethioninamine | >1.33 | 1.33 to 0.76 | — | <0.76 |
| betaine | >1.33 | 1.33 to 0.75 | — | <0.75 |
| dihydrobiopterin | >1.33 | 1.33 to 0.73 | — | <0.73 |
| methylmalonate (MMA) | >1.34 | 1.34 to 0.89 | — | <0.89 |
| 2-methylbutyrylglycine | >1.34 | 1.34 to 0.75 | — | <0.75 |
| glycerophosphoglycerol | >1.35 | 1.35 to 0.79 | — | <0.79 |
| cadaverine | >1.36 | 1.36 to 0.77 | — | <0.77 |
| glucuronide of C10H18O2 (11) | >1.41 | 1.41 to 0.77 | — | <0.77 |

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of enabling treatment or slowing progression of chronic kidney disease in a feline, the method comprising:

(a) diagnosing chronic kidney disease (CKD) in the feline by (i) measuring a normalized relative abundance of a first urine biomarker selected from the urine biomarkers listed in Table 1 or Table 2:

TABLE 1

| Urine Biomarker | Late-Stage CKD | Indeterminate Stage | Early-Stage Stage | Non-CKD |
|---|---|---|---|---|
| | | Diagnostic Range (measured as normalized relative abundance) | | |
| Sulfate | <−1.32 | −1.319 to −0.58 | −0.579 to 0.20 | >0.21 |
| N-acetylglucosamine/N-acetylgalactosamine | <−1.41 | −1.4 to −0.61 | −0.60 to 0.20 | >0.21 |
| hydroxyasparagine | <−1.29 | −1.28 to −0.55 | −0.54 to 0.40 | >0.41 |
| serine | <−1.32 | −1.31 to −0.74 | −0.739 to 0.40 | >0.41 |
| urea | <−1.32 | −1.31 to −0.73 | −0.72 to 0.30 | >0.31 |
| 1-methylnicotinamide | <−1.04 | −1.03 to −0.71 | −0.72 to 0.40 | >0.41 |
| fructose | <−1.06 | −1.05 to −0.75 | −0.74 to 0.40 | >0.41 |
| 3-methylhistidine | — | — | −0.77 to 0.50 | >0.51 |
| pimelate | <−1.3 | −1.29 to −0.64 | −0.63 to 0.20 | >0.21 |
| 4-acetylphenol sulfate | <−1.1 | −1.09 to −0.68 | −0.67 to 0.30 | >0.31 |
| N-acetyltryptophan | <−1.07 | −1.06 to −0.75 | −0.74 to 0.1 | >0.11 |

TABLE 1-continued

| Urine Biomarker | Diagnostic Range (measured as normalized relative abundance) | | | |
| | Late-Stage CKD | Indeterminate Stage | Early-Stage Stage | Non-CKD |
| --- | --- | --- | --- | --- |
| stachydrine | <−1.5 | −1.4 to −0.88 | −0.87 to 0.30 | >0.31 |
| felinine | <−1.4 | −1.39 to −0.64 | −0.63 to 0.35 | >0.36 |
| N4-acetylcytidine | <−0.92 | −0.91 to 0.00 | 0.01 to 0.30 | >0.31 |
| 2-methylmalonylcarnitine | <−0.57 | −0.56 to −0.38 | −0.37 to 0.32 | >0.33 |
| 4-vinylphenol sulfate | <−1.35 | −1.34 to −0.60 | −0.59 to 0.40 | >0.41 |
| dimethylarginine (SDMA + ADMA) | <−1.2 | −1.1 to −0.74 | −0.73 to 0.43 | >0.44 |
| N2,N2-dimethylguanine | <−1.1 | −1.1 to −0.65 | −0.64 to 0.40 | >0.41 |
| N6-methyllysine | <−1.4 | −1.3 to −0.62 | −0.61 to 0.20 | >0.21 |
| equol sulfate | — | — | −0.72 to 0.30 | >0.31 |
| prolylglycine | <−1.2 | −1.1 to −0.85 | −0.84 to 0.20 | >0.21 |
| O-sulfo-L-tyrosine | <−1.5 | −1.4 to −0.56 | −0.55 to 0.50 | >0.51 |
| N6,N6-dimethyllysine | <−1.24 | −1.23 to −1.17 | −1.16 to 0.30 | >0.31 |
| dihydrocaffeate sulfate (2) | <−0.89 | −0.88 to −0.60 | −0.59 to −0.36 | >0.361 |
| 2,6-dihydroxybenzoic acid | <−0.86 | −0.85 to −0.63 | −0.62 to 0.25 | >0.26 |
| picolinoylglycine | <−1.1 | −1.0 to −0.79 | −0.78 to 0.20 | >0.21 |
| vanillic acid glycine | <−0.77 | −0.76 to −0.63 | −0.62 to 0.20 | >0.21 |
| guanosine | <−1.1 | −1.0 to −0.55 | −0.54 to 0.43 | >0.431 |
| N-acetylalanine | <−1.22 | −1.21 to −0.54 | −0.53 to 0.0 | >0.1 |
| urate | <−1.34 | −1.33 to −0.58 | −0.57 to 0.40 | >0.41 |
| azelate | <−1.24 | −1.23 to −0.91 | −0.90 to 0.0 | >0.01 |
| arginine | <−1.34 | −1.33 to −0.72 | −0.71 to 0.49 | >0.50 |
| nicotinamide | <−1.4 | −1.3 to −0.74 | −0.73 to 0.20 | >0.21 |
| ornithine | <−1.32 | −1.31 to −1.0 | −0.99 to 0.30 | >0.31 |
| orotate | <−1.53 | −1.52 to −0.50 | −0.49 to 0.32 | >0.33 |
| trans-urocanate | <−1.44 | −1.43 to −0.78 | −0.77 to 0.35 | >0.36 |
| N-acetylglutamate | <−1.2 | −1.1 to −0.87 | −0.86 to 0.30 | >0.31 |
| ribitol | <−1.39 | −1.38 to −0.27 | −0.26 to 0.40 | >0.41 |
| indolelactate | <−1.13 | −1.12 to −0.81 | −0.80 to 0.20 | >0.21 |
| maleate | <−1.0 | — | −0.99 to 0.10 | >0.11 |
| cysteine s-sulfate | <−0.88 | −0.87 to −0.18 | −0.17 to 0.10 | >0.11 |
| 1-methylhistamine | <−0.79 | −0.78 to −0.16 | −0.15 to 0.33 | >0.34 |
| 4-hydroxyhippurate | <−1.23 | −1.22 to −0.90 | −0.89 to 0.10 | >0.11 |
| isovalerylglycine | <−1.2 | −1.1 to −0.94 | −0.93 to 0.20 | >0.21 |
| 7-methylguanine | <−1.3 | −1.2 to −0.56 | −0.55 to 0.30 | >0.31 |
| N6-acetyllysine | <−1.3 | −1.2 to −0.60 | −0.59 to 0.24 | >0.25 |
| pyrraline | <−0.49 | −0.48 to −0.36 | −0.35 to 0.20 | >0.21 |
| N6-carboxymethyllysine | <−1.2 | −1.1 to −0.83 | −0.82 to 0.30 | >0.31 |
| cyclo(gly-pro) | <−1.17 | — | −1.16 to 0.35 | >0.36 |
| 2-hydroxyglutarate | <−1.21 | −1.20 to −0.91 | −0.90 to 0.0 | >0.1 |
| N-acetyl-cadaverine | <−1.3 | −1.2 to −0.31 | −0.30 to 0.34 | >0.35 |
| felinylglycine | <−1.1 | −1.0 to −0.91 | −0.90 to 0.10 | >0.11 |
| 2-piperidinone | <−1.1 | −1.0 to −0.66 | −0.65 to 0.17 | >0.18 |
| 3-acetylphenol sulfate | <−1.03 | −1.02 to −1.01 | −1.0 to 0.20 | >0.21 |
| methionine sulfone | <−0.72 | −0.71 to −0.20 | −0.19 to 0.35 | >0.36 |
| fructosyllysine | <−1.0 | −0.99 to −0.86 | −0.85 to 0.30 | >0.31 |
| 4-vinylguaiacol sulfate | <−1.4 | −1.3 to −0.60 | −0.59 to 0.40 | >0.41 |
| 4-methoxyphenol sulfate | — | — | 0.61 to 0.45 | >0.451 |
| daidzein sulfate (2) | — | — | −0.82 to 0.30 | >0.31 |
| 3-methoxycatechol sulfate (2) | <−1.15 | −1.14 to −0.67 | −0.66 to 0.50 | >0.51 |
| N-acetylkynurenine (2) | <−1.1 | −1.0 to −0.62 | −0.61 to 0.10 | >0.11 |
| arabitol/xylitol | <−1.35 | −1.34 to −0.75 | −0.74 to 0.30 | >0.31 |
| indoleacetylglycine | <−1.2 | −1.1 to −0.55 | −0.54 to 0.24 | >0.25 |
| 3-amino-2-piperidone | <−1.4 | −1.3 to −1.2 | −1.1 to 0.30 | >0.31 |
| 5-hydroxy-2-methylpyridine sulfate | <−1.1 | −1.0 to −0.47 | −0.46 to 0.02 | >0.03 |
| 4-vinylcatechol sulfate | <−1.0 | −0.99 to −0.60 | −0.59 to 0.40 | >0.41 |
| oxindolylalanine | <−1.0 | — | −0.99 to 0.10 | >0.11 |
| N1-methyladenosine | <−1.21 | −1.20 to −0.49 | −0.48 to 0.35 | >0.36 |
| choline | <−1.0 | −0.99 to −0.86 | −0.85 to 0.20 | >0.21 |
| 3-phosphoglycerate | <−0.96 | −0.95 to −0.83 | −0.82 to 0.40 | >0.41 |
| N('1)-acetylspermidine | <−1.1 | −1.0 to −0.82 | −0.81 to 0.39 | >0.40 |
| ethylmalonate | <−1.15 | −1.14 to −0.66 | −0.65 to 0.30 | >0.31 |
| guanidinoacetate | <−1.39 | −1.38 to −0.87 | −0.86 to 0.65 | >0.64 |
| allantoin | <−1.34 | −1.33 to −0.68 | −0.67 to 0.36 | >0.37 |

TABLE 2

| Urine Biomarker | Non-CKD | Diagnostic Range (measured as normalized relative abundance) | | |
| --- | --- | --- | --- | --- |
| | | Early-Stage Stage | Indeterminate Stage | Late-Stage CKD |
| 1-methylguanidine | <0.72 | 0.72 to 1.41 | — | >1.41 |
| 4-ureidobutyrate | <0.77 | 0.77 to 1.38 | — | >1.38 |
| 1-methyl-5-imidazolelactate | <0.78 | 0.78 to 1.39 | — | >1.39 |
| scyllo-inositol | <0.79 | 0.79 to 1.28 | — | >1.28 |
| fucitol | <0.8 | 0.8 to 1.29 | — | >1.29 |
| N-acetyl-1-methylhistidine | <0.82 | 0.82 to 1.43 | — | >1.43 |
| arachidonate (20:4n6) | <0.83 | 0.83 to 1.47 | — | >1.47 |
| N-formylanthranilic acid | <0.83 | 0.83 to 1.36 | — | >1.36 |
| N-acetyl-isoputreanine | <0.85 | 0.85 to 1.34 | — | >1.34 |
| 3-methylglutarylcarnitine (2) | <0.86 | 0.86 to 1.35 | — | >1.35 |
| 2-O-methylascorbic acid | <0.87 | 0.87 to 1.42 | — | >1.42 |
| furaneol sulfate | <0.87 | 0.87 to 1.32 | — | >1.32 |
| glucuronate | <0.88 | 0.88 to 1.49 | — | >1.49 |
| citrate | <0.88 | 0.88 to 1.34 | — | >1.34 |
| benzoate | <0.88 | 0.88 to 1.31 | — | >1.31 |
| indolin-2-one | <0.88 | 0.88 to 1.28 | — | >1.28 |
| nicotinamide N-oxide | <0.89 | 0.89 to 1.47 | — | >1.47 |
| carboxyethyl-GABA | <0.9 | 0.9 to 1.44 | — | >1.44 |
| lyxonate | <0.9 | 0.9 to 1.34 | — | >1.34 |
| glucose | <0.9 | 0.9 to 1.69 | — | >1.69 |
| dimethylguanidino valeric acid (DMGV) | <0.91 | 0.91 to 1.43 | — | >1.43 |
| isocitrate | <0.91 | 0.91 to 1.42 | — | >1.42 |
| allantoic acid | <0.91 | 0.91 to 1.91 | — | >1.91 |
| 1-methyladenine | <0.92 | 0.92 to 1.46 | — | >1.46 |
| N-acetyltaurine | <0.92 | 0.92 to 1.44 | — | >1.44 |
| trimethylamine N-oxide | <0.92 | 0.92 to 1.41 | — | >1.41 |
| 4-hydroxyphenylacetoylcarnitine | <0.92 | 0.92 to 1.38 | — | >1.38 |
| 1-methylhypoxanthine | <0.92 | 0.92 to 1.34 | — | >1.34 |
| N-acetylneuraminate | <0.92 | 0.92 to 1.92 | — | >1.92 |
| malonylcarnitine | <0.93 | 0.93 to 1.5 | — | >1.5 |
| nicotinamide riboside | <0.93 | 0.93 to 1.47 | — | >1.47 |
| pimeloylcarnitine/3-methyladipoylcarnitine (C7-DC) | <0.93 | 0.93 to 1.35 | — | >1.35 |
| N-glycolylneuraminate | <0.93 | 0.93 to 1.6 | — | >1.6 |
| azelaoyltaurine | <0.93 | 0.93 to 1.89 | — | >1.89 |
| 3-carboxyadipate | <0.94 | 0.94 to 1.37 | — | >1.37 |
| dimethyl sulfone | <0.94 | 0.94 to 1.31 | — | >1.31 |
| tartronate (hydroxymalonate) | <0.95 | 0.95 to 1.44 | — | >1.44 |
| ascorbic acid 3-sulfate | <0.95 | 0.95 to 1.38 | — | >1.38 |
| malate | <0.95 | 0.95 to 1.35 | — | >1.35 |
| isovalerylcarnitine (C5) | <0.95 | 0.95 to 1.31 | — | >1.31 |
| glutarylcarnitine (C5-DC) | <0.96 | 0.96 to 1.64 | — | >1.64 |
| guanidinosuccinate | <0.97 | 0.97 to 1.41 | — | >1.41 |
| 3'-sialyllactose | <0.97 | 0.97 to 1.35 | — | >1.35 |
| 3-ureidopropionate | <0.97 | 0.97 to 1.68 | — | >1.68 |
| N6-succinyladenosine | <0.98 | 0.98 to 1.38 | — | >1.38 |
| C-glycosyltryptophan | <0.98 | 0.98 to 1.67 | — | >1.67 |
| isobutyrylcarnitine (C4) | <0.99 | 0.99 to 1.37 | — | >1.37 |
| N1-methylinosine | <0.99 | 0.99 to 1.63 | — | >1.63 |
| cysteinylglycine | <1.01 | 1.01 to 1.43 | — | >1.43 |
| 5,6-dihydrouridine | <1.01 | 1.01 to 1.84 | — | >1.84 |
| pseudouridine | <1.01 | 1.01 to 1.83 | — | >1.83 |
| 5-methylthioribose | <1.01 | 1.01 to 1.53 | — | >1.53 |
| 3,4-methylenevaleroylglycine | <1.02 | 1.02 to 1.42 | — | >1.42 |
| cysteine-glutathione disulfide | <1.02 | 1.02 to 1.52 | — | >1.52 |
| N-methylpipecolate | <1.03 | 1.03 to 1.43 | — | >1.43 |
| 7-methylurate | <1.03 | 1.03 to 1.32 | — | >1.32 |
| ribonate | <1.03 | 1.03 to 1.55 | — | >1.55 |
| N1-Methyl-2-pyridone-5-carboxamide | <1.04 | 1.04 to 1.66 | — | >1.66 |
| 1-methyl-4-imidazoleacetate | <1.05 | 1.05 to 1.56 | — | >1.56 |
| S-methylcysteine | <1.06 | 1.06 to 1.38 | — | >1.38 |
| creatinine | <1.07 | 1.07 to 2.03 | — | >2.03 |
| N-acetylserine | <1.1 | 1.1 to 1.54 | — | >1.54 |
| pyridoxate | <1.11 | 1.11 to 1.38 | — | >1.38 |
| gulonate | <1.11 | 1.11 to 1.47 | — | >1.47 |
| N-carbamoylputrescine | <1.14 | 1.14 to 1.65 | — | >1.65 |
| norvaline | <1.17 | 1.17 to 1.42 | — | >1.42 |
| tryptophan | >1.05 | 1.05 to 0.73 | — | <0.73 |
| phenyllactate (PLA) | >1.08 | 1.08 to 0.71 | — | <0.71 |
| dihydroorotate | >1.1 | 1.1 to 0.67 | — | <0.67 |
| N-acetylglycine | >1.11 | 1.11 to 0.64 | — | <0.64 |
| beta-guanidinopropanoate | >1.11 | 1.11 to 0.64 | — | <0.64 |

TABLE 2-continued

| Urine Biomarker | Non-CKD | Early-Stage Stage | Indeterminate Stage | Late-Stage CKD |
|---|---|---|---|---|
| 5-oxoproline | >1.12 | 1.12 to 0.62 | — | <0.62 |
| 5-hydroxylysine | >1.13 | 1.13 to 0.61 | — | <0.61 |
| cholate | >1.14 | 1.14 to 0.62 | — | <0.62 |
| azelate (C9-DC) | >1.16 | 1.16 to 0.61 | — | <0.61 |
| N-acetylvaline | >1.22 | 1.22 to 0.77 | — | <0.77 |
| glycylvaline | >1.23 | 1.23 to 0.77 | — | <0.77 |
| heptanoylglutamine | >1.23 | 1.23 to 0.76 | — | <0.76 |
| isovalerate (i5:0) | >1.26 | 1.26 to 0.75 | — | <0.75 |
| butyrylputrescine/isobutyrylputrescine | >1.28 | 1.28 to 0.77 | — | <0.77 |
| homoarginine | >1.28 | 1.28 to 0.77 | — | <0.77 |
| homostachydrine | >1.28 | 1.28 to 0.75 | — | <0.75 |
| N6-methyladenosine | >1.28 | 1.28 to 0.75 | — | <0.75 |
| 3-methoxytyramine | >1.29 | 1.29 to 0.91 | — | <0.91 |
| N-acetylhistamine | >1.29 | 1.29 to 0.79 | — | <0.79 |
| ferulylglycine (1) | >1.29 | 1.29 to 0.78 | — | <0.78 |
| S-methylcysteine sulfoxide | >1.3 | 1.3 to 0.84 | — | <0.84 |
| cyclo(pro-tyr) | >1.3 | 1.3 to 0.75 | — | <0.75 |
| N-lactoyl leucine | >1.31 | 1.31 to 0.74 | — | <0.74 |
| histamine | >1.31 | 1.31 to 0.72 | — | <0.72 |
| gamma-glutamylglycine | >1.31 | 1.31 to 0.73 | — | <0.73 |
| putrescine | >1.32 | 1.32 to 0.78 | — | <0.78 |
| alanyllysine | >1.32 | 1.32 to 0.74 | — | <0.74 |
| chenodeoxycholic acid sulfate (2) | >1.32 | 1.32 to 0.74 | — | <0.74 |
| N2,N2-dimethylguanosine | >1.33 | 1.33 to 0.77 | — | <0.77 |
| S-adenosylmethioninamine | >1.33 | 1.33 to 0.76 | — | <0.76 |
| betaine | >1.33 | 1.33 to 0.75 | — | <0.75 |
| dihydrobiopterin | >1.33 | 1.33 to 0.73 | — | <0.73 |
| methylmalonate (MMA) | >1.34 | 1.34 to 0.89 | — | <0.89 |
| 2-methylbutyrylglycine | >1.34 | 1.34 to 0.75 | — | <0.75 |
| glycerophosphoglycerol | >1.35 | 1.35 to 0.79 | — | <0.79 |
| cadaverine | >1.36 | 1.36 to 0.77 | — | <0.77 |
| glucuronide of C10H18O2 (11) | >1.41 | 1.41 to 0.77 | — | <0.77 | and (ii) determining that the feline has CKD if the normalized relative abundance of the first urine biomarker has a value outside the range under the non-CKD column, determining that the feline has early-stage chronic kidney disease if the normalized relative abundance of the first urine biomarker has a value in the range under the early-stage CKD column, or determining that the feline has late-stage CKD if the normalized relative abundance of the first urine biomarker has a value in the range under the late-stage CKD column; and (b) recommending a composition for the feline, wherein the composition treats or slows the progression of CKD in the feline, wherein the composition includes a combination of glycine, methionine, cysteine and glutamine.

2. The method of claim 1, wherein the composition comprises medium chain triglycerides.

3. A method of enabling treatment or slowing progression of chronic kidney disease in a feline, the method comprising:

(a) diagnosing chronic kidney disease (CKD) in the feline by (i) measuring a normalized relative abundance of a first urine biomarker selected from the urine biomarkers listed in Table 1 or Table 2:

TABLE 1

| Urine Biomarker | Late-Stage CKD | Indeterminate Stage | Early-Stage Stage | Non-CKD |
|---|---|---|---|---|
| Sulfate | <−1.32 | −1.319 to −0.58 | −0.579 to 0.20 | >0.21 |
| N-acetylglucosamine/ N-acetylgalactosamine | <−1.41 | −1.4 to −0.61 | −0.60 to 0.20 | >0.21 |
| hydroxyasparagine | <−1.29 | −1.28 to −0.55 | −0.54 to 0.40 | >0.41 |
| serine | <−1.32 | −1.31 to −0.74 | −0.739 to 0.40 | >0.41 |
| urea | <−1.32 | −1.31 to −0.73 | −0.72 to 0.30 | >0.31 |
| 1-methylnicotinamide | <−1.04 | −1.03 to −0.71 | −0.72 to 0.40 | >0.41 |
| fructose | <−1.06 | −1.05 to −0.75 | −0.74 to 0.40 | >0.41 |
| 3-methylhistidine | — | — | −0.77 to 0.50 | >0.51 |
| pimelate | <−1.3 | −1.29 to −0.64 | −0.63 to 0.20 | >0.21 |
| 4-acetylphenol sulfate | <−1.1 | −1.09 to −0.68 | −0.67 to 0.30 | >0.31 |
| N-acetyltryptophan | <−1.07 | −1.06 to −0.75 | −0.74 to 0.1 | >0.11 |
| stachydrine | <−1.5 | −1.4 to −0.88 | −0.87 to 0.30 | >0.31 |
| felinine | <−1.4 | −1.39 to −0.64 | −0.63 to 0.35 | >0.36 |

TABLE 1-continued

| Urine Biomarker | Diagnostic Range (measured as normalized relative abundance) | | | |
|---|---|---|---|---|
| | Late-Stage CKD | Indeterminate Stage | Early-Stage Stage | Non-CKD |
| N4-acetylcytidine | <−0.92 | −0.91 to 0.00 | 0.01 to 0.30 | >0.31 |
| 2-methylmalonyl-carnitine | <−0.57 | −0.56 to −0.38 | −0.37 to 0.32 | >0.33 |
| 4-vinylphenol sulfate | <−1.35 | −1.34 to −0.60 | −0.59 to 0.40 | >0.41 |
| dimethylarginine (SDMA + ADMA) | <−1.2 | −1.1 to −0.74 | −0.73 to 0.43 | >0.44 |
| N2,N2-dimethylguanine | <−1.1 | −1.1 to −0.65 | −0.64 to 0.40 | >0.41 |
| N6-methyllysine | <−1.4 | −1.3 to −0.62 | −0.61 to 0.20 | >0.21 |
| equol sulfate | — | — | −0.72 to 0.30 | >0.31 |
| prolylglycine | <−1.2 | −1.1 to −0.85 | −0.84 to 0.20 | >0.21 |
| O-sulfo-L-tyrosine | <−1.5 | −1.4 to −0.56 | −0.55 to 0.50 | >0.51 |
| N6,N6-dimethyllysine | <−1.24 | −1.23 to −1.17 | −1.16 to 0.30 | >0.31 |
| dihydrocaffeate sulfate (2) | <−0.89 | −0.88 to −0.60 | −0.59 to −0.36 | >0.361 |
| 2,6-dihydroxybenzoic acid | <−0.86 | −0.85 to −0.63 | −0.62 to 0.25 | >0.26 |
| picolinoylglycine | <−1.1 | −1.0 to −0.79 | −0.78 to 0.20 | >0.21 |
| vanillic acid glycine | <−0.77 | −0.76 to −0.63 | −0.62 to 0.20 | >0.21 |
| guanosine | <−1.1 | −1.0 to −0.55 | −0.54 to 0.43 | >0.431 |
| N-acetylalanine | <−1.22 | −1.21 to −0.54 | −0.53 to 0.0 | >0.1 |
| urate | <−1.34 | −1.33 to −0.58 | −0.57 to 0.40 | >0.41 |
| azelate | <−1.24 | −1.23 to −0.91 | −0.90 to 0.0 | >0.01 |
| arginine | <−1.34 | −1.33 to −0.72 | −0.71 to 0.49 | >0.50 |
| nicotinamide | <−1.4 | −1.3 to −0.74 | −0.73 to 0.20 | >0.21 |
| ornithine | <−1.32 | −1.31 to −1.0 | −0.99 to 0.30 | >0.31 |
| orotate | <−1.53 | −1.52 to −0.50 | −0.49 to 0.32 | >0.33 |
| trans-urocanate | <−1.44 | −1.43 to −0.78 | −0.77 to 0.35 | >0.36 |
| N-acetylglutamate | <−1.2 | −1.1 to −0.87 | −0.86 to 0.30 | >0.31 |
| ribitol | <−1.39 | −1.38 to −0.27 | −0.26 to 0.40 | >0.41 |
| indolelactate | <−1.13 | −1.12 to −0.81 | −0.80 to 0.20 | >0.21 |
| maleate | <−1.0 | — | −0.99 to 0.10 | >0.11 |
| cysteine s-sulfate | <−0.88 | −0.87 to −0.18 | −0.17 to 0.10 | >0.11 |
| 1-methylhistamine | <−0.79 | −0.78 to −0.16 | −0.15 to 0.33 | >0.34 |
| 4-hydroxyhippurate | <−1.23 | −1.22 to −0.90 | −0.89 to 0.10 | >0.11 |
| isovalerylglycine | <−1.2 | −1.1 to −0.94 | −0.93 to 0.20 | >0.21 |
| 7-methylguanine | <−1.3 | −1.2 to −0.56 | −0.55 to 0.30 | >0.31 |
| N6-acetyllysine | <−1.3 | −1.2 to −0.60 | −0.59 to 0.24 | >0.25 |
| pyrraline | <−0.49 | −0.48 to −0.36 | −0.35 to 0.20 | >0.21 |
| N6-carboxymethyllysine | <−1.2 | −1.1 to −0.83 | −0.82 to 0.30 | >0.31 |
| cyclo(gly-pro) | <−1.17 | — | −1.16 to 0.35 | >0.36 |
| 2-hydroxyglutarate | <−1.21 | −1.20 to −0.91 | −0.90 to 0.0 | >0.1 |
| N-acetyl-cadaverine | <−1.3 | −1.2 to −0.31 | −0.30 to 0.34 | >0.35 |
| felinylglycine | <−1.1 | −1.0 to −0.91 | −0.90 to 0.10 | >0.11 |
| 2-piperidinone | <−1.1 | −1.0 to −0.66 | −0.65 to 0.17 | >0.18 |
| 3-acetylphenol sulfate | <−1.03 | −1.02 to −1.01 | −1.0 to 0.20 | >0.21 |
| methionine sulfone | <−0.72 | −0.71 to −0.20 | −0.19 to 0.35 | >0.36 |
| fructosyllysine | <−1.0 | −0.99 to −0.86 | −0.85 to 0.30 | >0.31 |
| 4-vinylguaiacol sulfate | <−1.4 | −1.3 to −0.60 | −0.59 to 0.40 | >0.41 |
| 4-methoxyphenol sulfate | — | — | 0.61 to 0.45 | >0.451 |
| daidzein sulfate (2) | — | — | −0.82 to 0.30 | >0.31 |
| 3-methoxycatechol sulfate (2) | <−1.15 | −1.14 to −0.67 | −0.66 to 0.50 | >0.51 |
| N-acetylkynurenine (2) | <−1.1 | −1.0 to −0.62 | −0.61 to 0.10 | >0.11 |
| arabitol/xylitol | <−1.35 | −1.34 to −0.75 | −0.74 to 0.30 | >0.31 |
| indoleacetylglycine | <−1.2 | −1.1 to −0.55 | −0.54 to 0.24 | >0.25 |
| 3-amino-2-piperidone | <−1.4 | −1.3 to −1.2 | −1.1 to 0.30 | >0.31 |
| 5-hydroxy-2-methylpyridine sulfate | <−1.1 | −1.0 to −0.47 | −0.46 to 0.02 | >0.03 |
| 4-vinylcatechol sulfate | <−1.0 | −0.99 to −0.60 | −0.59 to 0.40 | >0.41 |
| oxindolylalanine | <−1.0 | — | −0.99 to 0.10 | >0.11 |
| N1-methyladenosine | <−1.21 | −1.20 to −0.49 | −0.48 to 0.35 | >0.36 |
| choline | <−1.0 | −0.99 to −0.86 | −0.85 to 0.20 | >0.21 |
| 3-phosphoglycerate | <−0.96 | −0.95 to −0.83 | −0.82 to 0.40 | >0.41 |
| N('1)-acetylspermidine | <−1.1 | −1.0 to −0.82 | −0.81 to 0.39 | >0.40 |
| ethylmalonate | <−1.15 | −1.14 to −0.66 | −0.65 to 0.30 | >0.31 |
| guanidinoacetate | <−1.39 | −1.38 to −0.87 | −0.86 to 0.65 | >0.64 |
| allantoin | <−1.34 | −1.33 to −0.68 | −0.67 to 0.36 | >0.37 |

27

TABLE 2

| Urine Biomarker | Diagnostic Range (measured as normalized relative abundance) | | | |
|---|---|---|---|---|
| | Non-CKD | Early-Stage Stage | Indeterminate Stage | Late-Stage CKD |
| 1-methylguanidine | <0.72 | 0.72 to 1.41 | — | >1.41 |
| 4-ureidobutyrate | <0.77 | 0.77 to 1.38 | — | >1.38 |
| 1-methyl-5-imidazolelactate | <0.78 | 0.78 to 1.39 | — | >1.39 |
| scyllo-inositol | <0.79 | 0.79 to 1.28 | — | >1.28 |
| fucitol | <0.8 | 0.8 to 1.29 | — | >1.29 |
| N-acetyl-1-methylhistidine | <0.82 | 0.82 to 1.43 | — | >1.43 |
| arachidonate (20:4n6) | <0.83 | 0.83 to 1.47 | — | >1.47 |
| N-formylanthranilic acid | <0.83 | 0.83 to 1.36 | — | >1.36 |
| N-acetyl-isoputreanine | <0.85 | 0.85 to 1.34 | — | >1.34 |
| 3-methylglutarylcarnitine (2) | <0.86 | 0.86 to 1.35 | — | >1.35 |
| 2-O-methylascorbic acid | <0.87 | 0.87 to 1.42 | — | >1.42 |
| furaneol sulfate | <0.87 | 0.87 to 1.32 | — | >1.32 |
| glucuronate | <0.88 | 0.88 to 1.49 | — | >1.49 |
| citrate | <0.88 | 0.88 to 1.34 | — | >1.34 |
| benzoate | <0.88 | 0.88 to 1.31 | — | >1.31 |
| indolin-2-one | <0.88 | 0.88 to 1.28 | — | >1.28 |
| nicotinamide N-oxide | <0.89 | 0.89 to 1.47 | — | >1.47 |
| carboxyethyl-GABA | <0.9 | 0.9 to 1.44 | — | >1.44 |
| lyxonate | <0.9 | 0.9 to 1.34 | — | >1.34 |
| glucose | <0.9 | 0.9 to 1.69 | — | >1.69 |
| dimethylguanidino valeric acid (DMGV) | <0.91 | 0.91 to 1.43 | — | >1.43 |
| isocitrate | <0.91 | 0.91 to 1.42 | — | >1.42 |
| allantoic acid | <0.91 | 0.91 to 1.91 | — | >1.91 |
| 1-methyladenine | <0.92 | 0.92 to 1.46 | — | >1.46 |
| N-acetyltaurine | <0.92 | 0.92 to 1.44 | — | >1.44 |
| trimethylamine N-oxide | <0.92 | 0.92 to 1.41 | — | >1.41 |
| 4-hydroxyphenyl-acetoylcarnitine | <0.92 | 0.92 to 1.38 | — | >1.38 |
| 1-methylhypoxanthine | <0.92 | 0.92 to 1.34 | — | >1.34 |
| N-acetylneuraminate | <0.92 | 0.92 to 1.92 | — | >1.92 |
| malonylcarnitine | <0.93 | 0.93 to 1.5 | — | >1.5 |
| nicotinamide riboside | <0.93 | 0.93 to 1.47 | — | >1.47 |
| pimeloylcarnitine/3-methyladipoylcarnitine (C7-DC) | <0.93 | 0.93 to 1.35 | — | >1.35 |
| N-glycolylneuraminate | <0.93 | 0.93 to 1.6 | — | >1.6 |
| azelaoyltaurine | <0.93 | 0.93 to 1.89 | — | >1.89 |
| 3-carboxyadipate | <0.94 | 0.94 to 1.37 | — | >1.37 |
| dimethyl sulfone | <0.94 | 0.94 to 1.31 | — | >1.31 |
| tartronate (hydroxymalonate) | <0.95 | 0.95 to 1.44 | — | >1.44 |
| ascorbic acid 3-sulfate | <0.95 | 0.95 to 1.38 | — | >1.38 |
| malate | <0.95 | 0.95 to 1.35 | — | >1.35 |
| isovalerylcarnitine (C5) | <0.95 | 0.95 to 1.31 | — | >1.31 |
| glutarylcarnitine (C5-DC) | <0.96 | 0.96 to 1.64 | — | >1.64 |
| guanidinosuccinate | <0.97 | 0.97 to 1.41 | — | >1.41 |
| 3'-sialyllactose | <0.97 | 0.97 to 1.35 | — | >1.35 |
| 3-ureidopropionate | <0.97 | 0.97 to 1.68 | — | >1.68 |
| N6-succinyladenosine | <0.98 | 0.98 to 1.38 | — | >1.38 |
| C-glycosyltryptophan | <0.98 | 0.98 to 1.67 | — | >1.67 |
| isobutyrylcarnitine (C4) | <0.99 | 0.99 to 1.37 | — | >1.37 |
| N1-methylinosine | <0.99 | 0.99 to 1.63 | — | >1.63 |
| cysteinylglycine | <1.01 | 1.01 to 1.43 | — | >1.43 |
| 5,6-dihydrouridine | <1.01 | 1.01 to 1.84 | — | >1.84 |
| pseudouridine | <1.01 | 1.01 to 1.83 | — | >1.83 |
| 5-methylthioribose | <1.01 | 1.01 to 1.53 | — | >1.53 |
| 3,4-methylenevaleroylglycine | <1.02 | 1.02 to 1.42 | — | >1.42 |
| cysteine-glutathione disulfide | <1.02 | 1.02 to 1.52 | — | >1.52 |
| N-methylpipecolate | <1.03 | 1.03 to 1.43 | — | >1.43 |
| 7-methylurate | <1.03 | 1.03 to 1.32 | — | >1.32 |
| ribonate | <1.03 | 1.03 to 1.55 | — | >1.55 |
| N1-Methyl-2-pyridone-5-carboxamide | <1.04 | 1.04 to 1.66 | — | >1.66 |
| 1-methyl-4-imidazoleacetate | <1.05 | 1.05 to 1.56 | — | >1.56 |

28

TABLE 2-continued

| Urine Biomarker | Diagnostic Range (measured as normalized relative abundance) | | | |
|---|---|---|---|---|
| | Non-CKD | Early-Stage Stage | Indeterminate Stage | Late-Stage CKD |
| S-methylcysteine | <1.06 | 1.06 to 1.38 | — | >1.38 |
| creatinine | <1.07 | 1.07 to 2.03 | — | >2.03 |
| N-acetylserine | <1.1 | 1.1 to 1.54 | — | >1.54 |
| pyridoxate | <1.11 | 1.11 to 1.38 | — | >1.38 |
| gulonate | <1.11 | 1.11 to 1.47 | — | >1.47 |
| N-carbamoylputrescine | <1.14 | 1.14 to 1.65 | — | >1.65 |
| norvaline | <1.17 | 1.17 to 1.42 | — | >1.42 |
| tryptophan | >1.05 | 1.05 to 0.73 | — | <0.73 |
| phenyllactate (PLA) | >1.08 | 1.08 to 0.71 | — | <0.71 |
| dihydroorotate | >1.1 | 1.1 to 0.67 | — | <0.67 |
| N-acetylglycine | >1.11 | 1.11 to 0.64 | — | <0.64 |
| beta-guanidinopropanoate | >1.11 | 1.11 to 0.64 | — | <0.64 |
| 5-oxoproline | >1.12 | 1.12 to 0.62 | — | <0.62 |
| 5-hydroxylysine | >1.13 | 1.13 to 0.61 | — | <0.61 |
| cholate | >1.14 | 1.14 to 0.62 | — | <0.62 |
| azelate (C9-DC) | >1.16 | 1.16 to 0.61 | — | <0.61 |
| N-acetylvaline | >1.22 | 1.22 to 0.77 | — | <0.77 |
| glycylvaline | >1.23 | 1.23 to 0.77 | — | <0.77 |
| heptanoylglutamine | >1.23 | 1.23 to 0.76 | — | <0.76 |
| isovalerate (15:0) | >1.26 | 1.26 to 0.75 | — | <0.75 |
| butyrylputrescine/isobutyrylputrescine | >1.28 | 1.28 to 0.77 | — | <0.77 |
| homoarginine | >1.28 | 1.28 to 0.77 | — | <0.77 |
| homostachydrine | >1.28 | 1.28 to 0.75 | — | <0.75 |
| N6-methyladenosine | >1.28 | 1.28 to 0.75 | — | <0.75 |
| 3-methoxytyramine | >1.29 | 1.29 to 0.91 | — | <0.91 |
| N-acetylhistamine | >1.29 | 1.29 to 0.79 | — | <0.79 |
| ferulylglycine (1) | >1.29 | 1.29 to 0.78 | — | <0.78 |
| S-methylcysteine sulfoxide | >1.3 | 1.3 to 0.84 | — | <0.84 |
| cyclo(pro-tyr) | >1.3 | 1.3 to 0.75 | — | <0.75 |
| N-lactoyl leucine | >1.31 | 1.31 to 0.74 | — | <0.74 |
| histamine | >1.31 | 1.31 to 0.72 | — | <0.72 |
| gamma-glutamylglycine | >1.31 | 1.31 to 0.73 | — | <0.73 |
| putrescine | >1.32 | 1.32 to 0.78 | — | <0.78 |
| alanyllysine | >1.32 | 1.32 to 0.74 | — | <0.74 |
| chenodeoxycholic acid sulfate (2) | >1.32 | 1.32 to 0.74 | — | <0.74 |
| N2,N2-dimethylguanosine | >1.33 | 1.33 to 0.77 | — | <0.77 |
| S-adenosylmethioninamine | >1.33 | 1.33 to 0.76 | — | <0.76 |
| betaine | >1.33 | 1.33 to 0.75 | — | <0.75 |
| dihydrobiopterin | >1.33 | 1.33 to 0.73 | — | <0.73 |
| methylmalonate (MMA) | >1.34 | 1.34 to 0.89 | — | <0.89 |
| 2-methylbutyrylglycine | >1.34 | 1.34 to 0.75 | — | <0.75 |
| glycerophosphoglycerol | >1.35 | 1.35 to 0.79 | — | <0.79 |
| cadaverine | >1.36 | 1.36 to 0.77 | — | <0.77 |
| glucuronide of C10H18O2 (11) | >1.41 | 1.41 to 0.77 | — | <0.77 | and (ii) determining that the feline has CKD if the normalized relative abundance of the first urine biomarker has a value outside the range under the non-CKD column, determining that the feline has early-stage chronic kidney disease if the normalized relative abundance of the first urine biomarker has a value in the range under the early-stage CKD column, or determining that the feline has late-stage CKD if the normalized relative abundance of the first urine biomarker has a value in the range under the late-stage CKD column; and (b) recommending a composition for the feline, wherein the composition treats or slows the progression of CKD in the feline, wherein the composition comprises arginine, eicosapentaenoic acid, docosahexaenoic acid, vitamin E, and B vitamins.

4. A method of enabling treatment or slowing progression of chronic kidney disease in a feline, the method comprising:

(a) diagnosing chronic kidney disease (CKD) in the feline by (i) measuring a normalized relative abundance of a first urine biomarker selected from the urine biomarkers listed in Table 1 or Table 2:

TABLE 1

| Urine Biomarker | Diagnostic Range (measured as normalized relative abundance) | | | |
|---|---|---|---|---|
| | Late-Stage CKD | Indeterminate Stage | Early-Stage Stage | Non-CKD |
| Sulfate | <−1.32 | −1.319 to −0.58 | −0.579 to 0.20 | >0.21 |
| N-acetylglucosamine/ N-acetylgalactosamine | <−1.41 | −1.4 to −0.61 | −0.60 to 0.20 | >0.21 |
| hydroxyasparagine | <−1.29 | −1.28 to −0.55 | −0.54 to 0.40 | >0.41 |
| serine | <−1.32 | −1.31 to −0.74 | −0.739 to 0.40 | >0.41 |
| urea | <−1.32 | −1.31 to −0.73 | −0.72 to 0.30 | >0.31 |
| 1-methylnicotinamide | <−1.04 | −1.03 to −0.71 | −0.72 to 0.40 | >0.41 |
| fructose | <−1.06 | −1.05 to −0.75 | −0.74 to 0.40 | >0.41 |
| 3-methylhistidine | — | — | −0.77 to 0.50 | >0.51 |
| pimelate | <−1.3 | −1.29 to −0.64 | −0.63 to 0.20 | >0.21 |
| 4-acetylphenol sulfate | <−1.1 | −1.09 to −0.68 | −0.67 to 0.30 | >0.31 |
| N-acetyltryptophan | <−1.07 | −1.06 to −0.75 | −0.74 to 0.1 | >0.11 |
| stachydrine | <−1.5 | −1.4 to −0.88 | −0.87 to 0.30 | >0.31 |
| felinine | <−1.4 | −1.39 to −0.64 | −0.63 to 0.35 | >0.36 |
| N4-acetylcytidine | <−0.92 | −0.91 to 0.00 | −0.01 to 0.30 | >0.31 |
| 2-methylmalonyl-carnitine | <−0.57 | −0.56 to −0.38 | −0.37 to 0.32 | >0.33 |
| 4-vinylphenol sulfate | <−1.35 | −1.34 to −0.60 | −0.59 to 0.40 | >0.41 |
| dimethylarginine (SDMA + ADMA) | <−1.2 | −1.1 to −0.74 | −0.73 to 0.43 | >0.44 |
| N2,N2-dimethylguanine | <−1.1 | −1.1 to −0.65 | −0.64 to 0.40 | >0.41 |
| N6-methyllysine | <−1.4 | −1.3 to −0.62 | −0.61 to 0.20 | >0.21 |
| equol sulfate | — | — | −0.72 to 0.30 | >0.31 |
| prolylglycine | <−1.2 | −1.1 to −0.85 | −0.84 to 0.20 | >0.21 |
| O-sulfo-L-tyrosine | <−1.5 | −1.4 to −0.56 | −0.55 to 0.50 | >0.51 |
| N6,N6-dimethyllysine | <−1.24 | −1.23 to −1.17 | −1.16 to 0.30 | >0.31 |
| dihydrocaffeate sulfate (2) | <−0.89 | −0.88 to −0.60 | −0.59 to −0.36 | >0.361 |
| 2,6-dihydroxybenzoic acid | <−0.86 | −0.85 to −0.63 | −0.62 to 0.25 | >0.26 |
| picolinoylglycine | <−1.1 | −1.0 to −0.79 | −0.78 to 0.20 | >0.21 |
| vanillic acid glycine | <−0.77 | −0.76 to −0.63 | −0.62 to 0.20 | >0.21 |
| guanosine | <−1.1 | −1.0 to −0.55 | −0.54 to 0.43 | >0.431 |
| N-acetylalanine | <−1.22 | −1.21 to −0.54 | −0.53 to 0.0 | >0.1 |
| urate | <−1.34 | −1.33 to −0.58 | −0.57 to 0.40 | >0.41 |
| azelate | <−1.24 | −1.23 to −0.91 | −0.90 to 0.0 | >0.01 |
| arginine | <−1.34 | −1.33 to −0.72 | −0.71 to 0.49 | >0.50 |
| nicotinamide | <−1.4 | −1.3 to −0.74 | −0.73 to 0.20 | >0.21 |
| ornithine | <−1.32 | −1.31 to −1.0 | −0.99 to 0.30 | >0.31 |
| orotate | <−1.53 | −1.52 to −0.50 | −0.49 to 0.32 | >0.33 |
| trans-urocanate | <−1.44 | −1.43 to −0.78 | −0.77 to 0.35 | >0.36 |
| N-acetylglutamate | <−1.2 | −1.1 to −0.87 | −0.86 to 0.30 | >0.31 |
| ribitol | <−1.39 | −1.38 to −0.27 | −0.26 to 0.40 | >0.41 |
| indolelactate | <−1.13 | −1.12 to −0.81 | −0.80 to 0.20 | >0.21 |
| maleate | <−1.0 | — | −0.99 to 0.10 | >0.11 |
| cysteine s-sulfate | <−0.88 | −0.87 to −0.18 | −0.17 to 0.10 | >0.11 |
| 1-methylhistamine | <−0.79 | −0.78 to −0.16 | −0.15 to 0.33 | >0.34 |
| 4-hydroxyhippurate | <−1.23 | −1.22 to −0.90 | −0.89 to 0.10 | >0.11 |
| isovalerylglycine | <−1.2 | −1.1 to −0.94 | −0.93 to 0.20 | >0.21 |
| 7-methylguanine | <−1.3 | −1.2 to −0.56 | −0.55 to 0.30 | >0.31 |
| N6-acetyllysine | <−1.3 | −1.2 to −0.60 | −0.59 to 0.24 | >0.25 |
| pyrraline | <−0.49 | −0.48 to −0.36 | −0.35 to 0.20 | >0.21 |
| N6-carboxymethyllysine | <−1.2 | −1.1 to −0.83 | −0.82 to 0.30 | >0.31 |
| cyclo(gly-pro) | <−1.17 | — | −1.16 to 0.35 | >0.36 |
| 2-hydroxyglutarate | <−1.21 | −1.20 to −0.91 | −0.90 to 0.0 | >0.1 |
| N-acetyl-cadaverine | <−1.3 | −1.2 to −0.31 | −0.30 to 0.34 | >0.35 |
| felinylglycine | <−1.1 | −1.0 to −0.91 | −0.90 to 0.10 | >0.11 |
| 2-piperidinone | <−1.1 | −1.0 to −0.66 | −0.65 to 0.17 | >0.18 |
| 3-acetylphenol sulfate | <−1.03 | −1.02 to −1.01 | −1.0 to 0.20 | >0.21 |
| methionine sulfone | <−0.72 | −0.71 to −0.20 | −0.19 to 0.35 | >0.36 |
| fructosyllysine | <−1.0 | −0.99 to −0.86 | −0.85 to 0.30 | >0.31 |
| 4-vinylguaiacol sulfate | <−1.4 | −1.3 to −0.60 | −0.59 to 0.40 | >0.41 |
| 4-methoxyphenol sulfate | — | — | −0.61 to 0.45 | >0.451 |
| daidzein sulfate (2) | — | — | −0.82 to 0.30 | >0.31 |

TABLE 1-continued

| | Diagnostic Range (measured as normalized relative abundance) | | | |
|---|---|---|---|---|
| Urine Biomarker | Late-Stage CKD | Indeterminate Stage | Early-Stage Stage | Non-CKD |
| 3-methoxycatechol sulfate (2) | <−1.15 | −1.14 to −0.67 | −0.66 to 0.50 | >0.51 |
| N-acetylkynurenine (2) | <−1.1 | −1.0 to −0.62 | −0.61 to 0.10 | >0.11 |
| arabitol/xylitol | <−1.35 | −1.34 to −0.75 | −0.74 to 0.30 | >0.31 |
| indoleacetylglycine | <−1.2 | −1.1 to −0.55 | −0.54 to 0.24 | >0.25 |
| 3-amino-2-piperidone | <−1.4 | −1.3 to −1.2 | −1.1 to 0.30 | >0.31 |
| 5-hydroxy-2-methylpyridine sulfate | <−1.1 | −1.0 to −0.47 | −0.46 to 0.02 | >0.03 |
| 4-vinylcatechol sulfate | <−1.0 | −0.99 to −0.60 | −0.59 to 0.40 | >0.41 |
| oxindolylalanine | <−1.0 | — | −0.99 to 0.10 | >0.11 |
| N1-methyladenosine | <−1.21 | −1.20 to −0.49 | −0.48 to 0.35 | >0.36 |
| choline | <−1.0 | −0.99 to −0.86 | −0.85 to 0.20 | >0.21 |
| 3-phosphoglycerate | <−0.96 | −0.95 to −0.83 | −0.82 to 0.40 | >0.41 |
| N('1)-acetylspermidine | <−1.1 | −1.0 to −0.82 | −0.81 to 0.39 | >0.40 |
| ethylmalonate | <−1.15 | −1.14 to −0.66 | −0.65 to 0.30 | >0.31 |
| guanidinoacetate | <−1.39 | −1.38 to −0.87 | −0.86 to 0.65 | >0.64 |
| allantoin | <−1.34 | −1.33 to −0.68 | −0.67 to 0.36 | >0.37 |

TABLE 2

| | Diagnostic Range (measured as normalized relative abundance) | | | |
|---|---|---|---|---|
| Urine Biomarker | Non-CKD | Early-Stage Stage | Indeterminate Stage | Late-Stage CKD |
| 1-methylguanidine | <0.72 | 0.72 to 1.41 | — | >1.41 |
| 4-ureidobutyrate | <0.77 | 0.77 to 1.38 | — | >1.38 |
| 1-methyl-5-imidazolelactate | <0.78 | 0.78 to 1.39 | — | >1.39 |
| scyllo-inositol | <0.79 | 0.79 to 1.28 | — | >1.28 |
| fucitol | <0.8 | 0.8 to 1.29 | — | >1.29 |
| N-acetyl-1-methylhistidine | <0.82 | 0.82 to 1.43 | — | >1.43 |
| arachidonate (20:4n6) | <0.83 | 0.83 to 1.47 | — | >1.47 |
| N-formylanthranilic acid | <0.83 | 0.83 to 1.36 | — | >1.36 |
| N-acetyl-isoputreanine | <0.85 | 0.85 to 1.34 | — | >1.34 |
| 3-methylglutarylcarnitine (2) | <0.86 | 0.86 to 1.35 | — | >1.35 |
| 2-O-methylascorbic acid | <0.87 | 0.87 to 1.42 | — | >1.42 |
| furaneol sulfate | <0.87 | 0.87 to 1.32 | — | >1.32 |
| glucuronate | <0.88 | 0.88 to 1.49 | — | >1.49 |
| citrate | <0.88 | 0.88 to 1.34 | — | >1.34 |
| benzoate | <0.88 | 0.88 to 1.31 | — | >1.31 |
| indolin-2-one | <0.88 | 0.88 to 1.28 | — | >1.28 |
| nicotinamide N-oxide | <0.89 | 0.89 to 1.47 | — | >1.47 |
| carboxyethyl-GABA | <0.9 | 0.9 to 1.44 | — | >1.44 |
| lyxonate | <0.9 | 0.9 to 1.34 | — | >1.34 |
| glucose | <0.9 | 0.9 to 1.69 | — | >1.69 |
| dimethylguanidino valeric acid (DMGV) | <0.91 | 0.91 to 1.43 | — | >1.43 |
| isocitrate | <0.91 | 0.91 to 1.42 | — | >1.42 |
| allantoic acid | <0.91 | 0.91 to 1.91 | — | >1.91 |
| 1-methyladenine | <0.92 | 0.92 to 1.46 | — | >1.46 |
| N-acetyltaurine | <0.92 | 0.92 to 1.44 | — | >1.44 |
| trimethylamine N-oxide | <0.92 | 0.92 to 1.41 | — | >1.41 |
| 4-hydroxyphenylacetoylcarnitine | <0.92 | 0.92 to 1.38 | — | >1.38 |
| 1-methylhypoxanthine | <0.92 | 0.92 to 1.34 | — | >1.34 |
| N-acetylneuraminate | <0.92 | 0.92 to 1.92 | — | >1.92 |
| malonylcarnitine | <0.93 | 0.93 to 1.5 | — | >1.5 |
| nicotinamide riboside | <0.93 | 0.93 to 1.47 | — | >1.47 |
| pimeloylcarnitine/3-methyladipoylcarnitine (C7-DC) | <0.93 | 0.93 to 1.35 | — | >1.35 |
| N-glycolylneuraminate | <0.93 | 0.93 to 1.6 | — | >1.6 |
| azelaoyltaurine | <0.93 | 0.93 to 1.89 | — | >1.89 |
| 3-carboxyadipate | <0.94 | 0.94 to 1.37 | — | >1.37 |
| dimethyl sulfone | <0.94 | 0.94 to 1.31 | — | >1.31 |
| tartronate (hydroxymalonate) | <0.95 | 0.95 to 1.44 | — | >1.44 |
| ascorbic acid 3-sulfate | <0.95 | 0.95 to 1.38 | — | >1.38 |
| malate | <0.95 | 0.95 to 1.35 | — | >1.35 |
| isovalerylcarnitine (C5) | <0.95 | 0.95 to 1.31 | — | >1.31 |
| glutarylcarnitine (C5-DC) | <0.96 | 0.96 to 1.64 | — | >1.64 |
| guanidinosuccinate | <0.97 | 0.97 to 1.41 | — | >1.41 |
| 3'-sialyllactose | <0.97 | 0.97 to 1.35 | — | >1.35 |

TABLE 2-continued

| Urine Biomarker | Diagnostic Range (measured as normalized relative abundance) | | | |
| | Non-CKD | Early-Stage Stage | Indeterminate Stage | Late-Stage CKD |
| --- | --- | --- | --- | --- |
| 3-ureidopropionate | <0.97 | 0.97 to 1.68 | — | >1.68 |
| N6-succinyladenosine | <0.98 | 0.98 to 1.38 | — | >1.38 |
| C-glycosyltryptophan | <0.98 | 0.98 to 1.67 | — | >1.67 |
| isobutyrylcarnitine (C4) | <0.99 | 0.99 to 1.37 | — | >1.37 |
| N1-methylinosine | <0.99 | 0.99 to 1.63 | — | >1.63 |
| cysteinylglycine | <1.01 | 1.01 to 1.43 | — | >1.43 |
| 5,6-dihydrouridine | <1.01 | 1.01 to 1.84 | — | >1.84 |
| pseudouridine | <1.01 | 1.01 to 1.83 | — | >1.83 |
| 5-methylthioribose | <1.01 | 1.01 to 1.53 | — | >1.53 |
| 3,4-methylenevaleroylglycine | <1.02 | 1.02 to 1.42 | — | >1.42 |
| cysteine-glutathione disulfide | <1.02 | 1.02 to 1.52 | — | >1.52 |
| N-methylpipecolate | <1.03 | 1.03 to 1.43 | — | >1.43 |
| 7-methylurate | <1.03 | 1.03 to 1.32 | — | >1.32 |
| ribonate | <1.03 | 1.03 to 1.55 | — | >1.55 |
| N1-Methyl-2-pyridone-5-carboxamide | <1.04 | 1.04 to 1.66 | — | >1.66 |
| 1-methyl-4-imidazoleacetate | <1.05 | 1.05 to 1.56 | — | >1.56 |
| S-methylcysteine | <1.06 | 1.06 to 1.38 | — | >1.38 |
| creatinine | <1.07 | 1.07 to 2.03 | — | >2.03 |
| N-acetylserine | <1.1 | 1.1 to 1.54 | — | >1.54 |
| pyridoxate | <1.11 | 1.11 to 1.38 | — | >1.38 |
| gulonate | <1.11 | 1.11 to 1.47 | — | >1.47 |
| N-carbamoylputrescine | <1.14 | 1.14 to 1.65 | — | >1.65 |
| norvaline | <1.17 | 1.17 to 1.42 | — | >1.42 |
| tryptophan | >1.05 | 1.05 to 0.73 | — | <0.73 |
| phenyllactate (PLA) | >1.08 | 1.08 to 0.71 | — | <0.71 |
| dihydroorotate | >1.1 | 1.1 to 0.67 | — | <0.67 |
| N-acetylglycine | >1.11 | 1.11 to 0.64 | — | <0.64 |
| beta-guanidinopropanoate | >1.11 | 1.11 to 0.64 | — | <0.64 |
| 5-oxoproline | >1.12 | 1.12 to 0.62 | — | <0.62 |
| 5-hydroxylysine | >1.13 | 1.13 to 0.61 | — | <0.61 |
| cholate | >1.14 | 1.14 to 0.62 | — | <0.62 |
| azelate (C9-DC) | >1.16 | 1.16 to 0.61 | — | <0.61 |
| N-acetylvaline | >1.22 | 1.22 to 0.77 | — | <0.77 |
| glycylvaline | >1.23 | 1.23 to 0.77 | — | <0.77 |
| heptanoylglutamine | >1.23 | 1.23 to 0.76 | — | <0.76 |
| isovalerate (i5:0) | >1.26 | 1.26 to 0.75 | — | <0.75 |
| butyrylputrescine/isobutyrylputrescine | >1.28 | 1.28 to 0.77 | — | <0.77 |
| homoarginine | >1.28 | 1.28 to 0.77 | — | <0.77 |
| homostachydrine | >1.28 | 1.28 to 0.75 | — | <0.75 |
| N6-methyladenosine | >1.28 | 1.28 to 0.75 | — | <0.75 |
| 3-methoxytyramine | >1.29 | 1.29 to 0.91 | — | <0.91 |
| N-acetylhistamine | >1.29 | 1.29 to 0.79 | — | <0.79 |
| ferulylglycine (1) | >1.29 | 1.29 to 0.78 | — | <0.78 |
| S-methylcysteine sulfoxide | >1.3 | 1.3 to 0.84 | — | <0.84 |
| cyclo(pro-tyr) | >1.3 | 1.3 to 0.75 | — | <0.75 |
| N-lactoyl leucine | >1.31 | 1.31 to 0.74 | — | <0.74 |
| histamine | >1.31 | 1.31 to 0.72 | — | <0.72 |
| gamma-glutamylglycine | >1.31 | 1.31 to 0.73 | — | <0.73 |
| putrescine | >1.32 | 1.32 to 0.78 | — | <0.78 |
| alanyllysine | >1.32 | 1.32 to 0.74 | — | <0.74 |
| chenodeoxycholic acid sulfate (2) | >1.32 | 1.32 to 0.74 | — | <0.74 |
| N2,N2-dimethylguanosine | >1.33 | 1.33 to 0.77 | — | <0.77 |
| S-adenosylmethioninamine | >1.33 | 1.33 to 0.76 | — | <0.76 |
| betaine | >1.33 | 1.33 to 0.75 | — | <0.75 |
| dihydrobiopterin | >1.33 | 1.33 to 0.73 | — | <0.73 |
| methylmalonate (MMA) | >1.34 | 1.34 to 0.89 | — | <0.89 |
| 2-methylbutyrylglycine | >1.34 | 1.34 to 0.75 | — | <0.75 |
| glycerophosphoglycerol | >1.35 | 1.35 to 0.79 | — | <0.79 |
| cadaverine | >1.36 | 1.36 to 0.77 | — | <0.77 |
| glucuronide of C10H18O2 (11) | >1.41 | 1.41 to 0.77 | — | <0.77 | and (ii) determining that the feline has CKD if the normalized relative abundance of the first urine biomarker has a value outside the range under the non-CKD column, determining that the feline has early-stage chronic kidney disease if the normalized relative abundance of the first urine biomarker has a value in the range under the early-stage CKD column, or determining that the feline has late-stage CKD if the normalized relative abundance of the first urine biomarker has a value in the range under the late-stage CKD column; and (b) recommending a composition for the feline, wherein the composition treats or slows the progression of CKD in the feline, wherein the composition contains less than 1% of potassium and contains less than 1% of phosphorous compounds and phosphate compounds.

5. The method of claim 1, wherein the composition has protein and phosphorus in a ratio between 5:1 and 15:1.

6. The method of claim 1, wherein the composition is a pet food composition or is administered in conjunction with a pet food composition.

7. The method of claim 3, wherein the composition comprises medium chain triglycerides.

8. The method of claim 4, wherein the composition comprises medium chain triglycerides.

\*    \*    \*    \*    \*